United States Patent
Pratt et al.

(10) Patent No.: US 8,801,909 B2
(45) Date of Patent: *Aug. 12, 2014

(54) POLYMETAL HYDROXYCHLORIDE PROCESSES AND COMPOSITIONS: ENHANCED EFFICACY ANTIPERSPIRANT SALT COMPOSITIONS

(75) Inventors: William E. Pratt, Morehead City, NC (US); Joseph J. Stevens, West Point, MS (US); Peter G. Symons, Williamsville, NY (US)

(73) Assignee: Nextchem, LLC, West Point, MO (US)

( * ) Notice: Subject to any disclaimer, the term of this patent is extended or adjusted under 35 U.S.C. 154(b) by 1744 days.

This patent is subject to a terminal disclaimer.

(21) Appl. No.: 11/619,478

(22) Filed: Jan. 3, 2007

(65) Prior Publication Data

US 2007/0196302 A1 Aug. 23, 2007

Related U.S. Application Data

(60) Provisional application No. 60/756,848, filed on Jan. 6, 2006, provisional application No. 60/829,793, filed on Oct. 17, 2006.

(51) Int. Cl.
*B01D 61/46* (2006.01)
(52) U.S. Cl.
USPC .......................................................... 204/529
(58) Field of Classification Search
USPC .......................................................... 204/529
See application file for complete search history.

(56) References Cited

U.S. PATENT DOCUMENTS

| | | | |
|---|---|---|---|
| 2,854,382 A | 9/1958 | Grad | |
| 3,113,911 A | 12/1963 | Jones | |
| 3,282,857 A * | 11/1966 | Fitch et al. | 516/90 |
| 3,767,549 A | 10/1973 | Sasaki et al. | |
| 4,147,605 A | 4/1979 | Schenker | |
| 4,203,822 A | 5/1980 | Schenker | |
| 4,331,609 A | 5/1982 | Orr | |
| 4,359,456 A | 11/1982 | Gosling | |
| 4,608,141 A | 8/1986 | Chlanda | |
| 4,775,478 A | 10/1988 | Voss | |

(Continued)

FOREIGN PATENT DOCUMENTS

| | | |
|---|---|---|
| CN | 1186773 | 7/1998 |
| CN | 1186773 A | 7/1998 |

(Continued)

OTHER PUBLICATIONS

Rosenberg, Richard; *Soap, Perfumery & Cosmetics*, (2000), vol. 7, pp. 26-28.

(Continued)

*Primary Examiner* — Arun S Phasge
(74) *Attorney, Agent, or Firm* — Fulbright & Jaworski LLP; Scott D. Rothenberger

(57) ABSTRACT

The invention describes processes for the production of basic aluminum compounds, including aluminum chlorohydrate, basic zirconium compounds, and basic aluminum zirconium compounds. The process produces products of a wide range of basicities. The products formed by the present invention are comprised of low molecular weight species characteristic of enhanced efficacy antiperspirant salt compositions. The products of this process are suitable for use as water purification agents, as binders in catalyst applications, and in antiperspirant applications. In addition, the invention is directed to the products made by the disclosed process.

83 Claims, 9 Drawing Sheets

Electrodialysis Stack Showing the Removal of Electrolyte, MX from Depleting Solution and the Concentration of MX in the Receiving Solution

(56) References Cited

U.S. PATENT DOCUMENTS

| | | | |
|---|---|---|---|
| 4,775,528 | A | 10/1988 | Callaghan |
| 4,871,525 | A | 10/1989 | Giovanniello |
| 5,064,538 | A | 11/1991 | Boeteng |
| 5,141,610 | A | 8/1992 | Vaughan |
| 5,202,115 | A | 4/1993 | Barr |
| 5,258,109 | A | 11/1993 | Vaughan |
| 5,264,097 | A | 11/1993 | Vaughan |
| 5,378,400 | A | 1/1995 | Parusel |
| 5,384,017 | A | 1/1995 | Lumbroso |
| 5,718,876 | A | 2/1998 | Parekh |
| 5,955,064 | A | 9/1999 | Giovanniello |
| 5,985,234 | A | 11/1999 | Dulko |
| 5,997,838 | A | 12/1999 | Dulko |
| 6,036,935 | A | 3/2000 | Dulko |
| 6,042,816 | A | 3/2000 | Shen |
| 6,149,897 | A | 11/2000 | Swaile |
| 6,245,325 | B1 | 6/2001 | Shen |
| 6,451,296 | B1 | 9/2002 | Li |
| 6,485,812 | B1 | 11/2002 | Sekiguchi |
| 6,649,152 | B2 | 11/2003 | Carrillo |
| 6,902,724 | B1 | 6/2005 | Parekh |
| 6,991,780 | B2 | 1/2006 | Carrillo |
| 7,846,318 | B2 * | 12/2010 | Pratt et al. ............... 205/208 |

FOREIGN PATENT DOCUMENTS

| | | |
|---|---|---|
| DE | 2310073 | 9/1973 |
| DE | 223424 | 6/1985 |
| FR | 2384861 A1 | 10/1978 |
| JP | 48055195 | 8/1973 |
| JP | 48060099 | 8/1973 |
| JP | 7-803 | 1/1995 |
| JP | 7-80253 | 3/1995 |
| RO | 63835 | 4/1979 |

OTHER PUBLICATIONS

Lu, Guang-jie; Zhongguo Huanjing Kexue, (2000), vol. 20(3), pp. 250-253, Abstract only.

Qu, Jiuhui; *Faming Zhuanli Shenqing Gongkai Shuominshu*, Derwent Abstract.

Rosenberg & Allan; *Soap, Perfumery & Cosmetics*, (1997), vol. 7, pp. 27-30.

White, D.A., *Journal of Membrane Science*, (1996), 113(2) 331-125:17950.

Terada, Ichiro; Garasau Kenkyu Hokoku, (1997), 4(1/2) 59-127:222385, Abstract only.

Office Action dated Mar. 24, 2009, (11 pgs.).

Amendment and Response to Office Action dated Mar. 24, 2009, dated Jun. 23, 2009 (15 pgs.).

Office Action dated Oct. 21, 2009 (13 pgs.).

Amendment and Response to Final Office Action of Oct. 21, 2009, dated Feb. 18, 2010 (16 pgs.).

Advisory Action dated Mar. 9, 2010 (3 pgs.).

Amendment and Response to Advisory Action of Mar. 9, 2010, dated Apr. 21, 2010 (12 pgs.).

Declaration of William Pratt, PH.D., under 37 CFR 1.132, with resume, dated Apr. 21, 2010 (11 pgs.).

* cited by examiner

Electrodialysis Stack Showing the Removal of Electrolyte, MX from Depleting Solution and the Concentration of MX in the Receiving Solution 40% PAC Solution Electrodialysis of 40% PAC
with Zirconium Hydroxychloride and Glycine

POLYMETAL HYDROXYCHLORIDE PROCESSES AND COMPOSITIONS: ENHANCED EFFICACY ANTIPERSPIRANT SALT COMPOSITIONS

CROSS REFERENCE TO RELATED APPLICATIONS

This application claims benefit under 35 U.S.C. §119(e) to U.S. Ser. No. 60/756,848, entitled "Process for Increasing the Basicity of Polymetal Halides", filed Jan. 6, 2006 by William E. Pratt and Joseph J. Stevens.

This application also claims benefit under 35 U.S.C. §119 (e) to U.S. Ser. No. 60/829,793, entitled "Polymetal Hydroxychloride Processes and Compositions: Enhanced Efficacy Antiperspirant Salt Compositions", filed Oct. 17, 2006 by William E. Pratt and Joseph J. Stevens, the contents this provisional application of which are incorporated herein by reference in their entirety.

BACKGROUND OF THE INVENTION

Polyaluminum chloride (PAC) is the name given to the family of compounds defined by the formula:

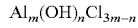

$$Al_m(OH)_nCl_{3m-n}$$

Where $0 < n \leq 3m$ and where $m \geq 1$. The degree of neutralization (i.e., the OH to Al ratio) is known as the basicity. In the case of polyaluminum chlorides the basicity is defined by the formula n/3 m. The highest basicity PAC of commercial interest is the polyaluminum chloride with 83% basicity known as aluminum chlorohydrate (ACH); it has an empirical formula of $Al_2(OH)_5Cl$.

High basicity, high purity PAC, including ACH, is commonly used either alone or in combination with zirconium hydroxyl-halides to produce antiperspirants. Polyaluminum chloride, including ACH used for this purpose is prepared by the reaction of hydrochloric acid or aluminum chloride or low-basicity PAC with aluminum metal. Thus, U.S. Pat. No. 6,245,325 states that the reaction of hydrochloric acid with aluminum metal is generally known and is the method generally utilized to prepare high basicity PAC and ACH solutions on a commercial basis. U.S. Pat. No. 6,902,724 and references contained therein teach the reaction of aluminum chloride with aluminum metal to produce aluminum antiperspirant salt compositions. U.S. Pat. No. 2,854,382, U.S. Pat. No. 4,331,609, U.S. Pat. No. 4,775,528, U.S. Pat. No. 5,955,064, U.S. Pat. No. 6,126,928 and U.S. Pat. No. 6,902,724 teach the preparation of aluminum-zirconium antiperspirant salt compositions whereby zirconium-hydroxyl chlorides are combined with high basicity PAC and or ACH that is prepared from aluminum metal as discussed above.

Aluminum metal is an expensive source of aluminum ion when compared to other sources of aluminum ion like aluminum trihydrate. Based on historical pricing relationships, aluminum from aluminum metal costs about three times as much as aluminum from aluminum trihydrate.

Aluminum and aluminum-zirconium antiperspirants have been known for several decades (see U.S. Pat. No. 2,854,382 (Grad), U.S. Pat. No. 4,331,609 (Orr) and U.S. Pat. No. 4,871,525 (Giovanniello) and references contained therein). These products typically contain an antiperspirant active in the form of an aluminum and/or zirconium salt; said salts are formed by partial neutralization of acidic aluminum ($Al^{+3}$) and/or zirconium ($Zr^{+4}$) metal ions.

The partial neutralization of these ions results in the formation of aluminum and zirconium hydrolysis products of complex structure. The performance (i.e., efficacy) of aluminum and aluminum-zirconium antiperspirant salt compositions is dependent on the molecular distribution of these hydrolysis products. In general, low molecular weight hydrolysis products favor better performance by providing increased sweat inhibition. Low molecular weight antiperspirant salt compositions which provide increased sweat inhibition are said to have enhanced efficacy.

Aluminum and aluminum-zirconium antiperspirants salts function by forming insoluble metal hydroxides in the ducts of sweat glands, this blockage prevents perspiration. Low molecular weight antiperspirant salts penetrate more deeply into these ducts than their high molecular weight counterparts. Thus, deeper penetration provides more effective blockage. (See Quatrale, et. al., The Mechanism of Antiperspirant Action of Aluminum Salts, Journal of the Society of Cosmetic Chemists, May-June 1981, 32:107-136 & Journal of the Society of Cosmetic Chemists, November-December 1985, 36:435-440).

High pressure liquid chromatography (HPLC) employing size exclusion columns is commonly used to characterize the molecular weight distribution and efficacy of aluminum and aluminum-zirconium antiperspirant salts. Size exclusion chromatographic columns have a high affinity for low molecular weight materials and a low affinity for high molecular weight materials. This difference in affinity causes high molecular weight materials to be eluted more quickly than low molecular weight materials. Accordingly, this HPLC technique separates and identifies the components of aluminum and aluminum-zirconium antiperspirant salts with respect to molecular weight. Five distinct species have been identified by this technique. The highest molecular weight species is eluted first and referred to as Peak 1 material. The lowest molecular weight species is eluted last and referred to as Peak 5 material. FIG. 2 shows a HPLC diagram of an aluminum antiperspirant salt. The relative area of each peak indicates the amount of the various components present. In this diagram Peaks 1 thru 3 have a greater relative area than Peaks 4 & 5, indicating that this sample is primarily composed of high molecular weight, low efficacy components. (In some references authors have used the term "band" instead of the term "peak" to describe the results of HPLC analysis. Generally, Bands I, II, III and IV of one system correspond to Peaks 1+2, (Band I), 3, 4, and 5 of the other system.)

Review of the literature shows that the low molecular weight species in Peak 4 and Peak 5 are responsible for increased sweat inhibition and that enhanced efficacy results when there is a preponderance of these peaks. These reports indicate there are at least two distinct groups of materials in which there is a preponderance of Peaks 4 and 5. These two groups of materials are referred to herein as Group 1 Materials and Group 2 Materials; both of which exhibit the attribute of enhanced efficacy. These two groups are differentiated with respect to their stability in water. As elaborated below, Group 1 Materials are unstable in water and decompose rapidly to high molecular weight low efficacy materials. Group 2 Materials are stable in water; this characteristic provides certain commercial benefits as explained below.

Group 1 Materials are characterized by their Peak 4 content in comparison to their Peak 3 content. A Peak 4 to Peak 3 area ratio of 0.5 or greater provides for increased sweat inhibition. These materials typically contain a preponderance of Peak 4 and a low level of Peak 3 and Peak 5. For example, 83% basic aluminum chlorohydrate (produced by the reaction of hydrochloric acid with aluminum metal) primarily contains high molecular weight species of Peaks 1 through 3. However ACH is converted to a Group 1 Material by heating a dilute solution (e.g. about a 10% salt concentration by weight) at about 80-100° C. for about 4 to 20 hours. (See U.S. Pat. No. 4,359,456 (Gosling), U.S. Pat. No. 4,775,528 (Callaghan), U.S. Pat. No. 5,955,064 (Giovanniello), U.S. Pat. No. 6,149,897 (Swaile) and references contained therein).

Table 1, Example 1 shows the composition of ACH with about 83% basicity prepared by the reaction of hydrochloric acid with aluminum metal. This material contains about 74% of high molecular weight species (Peaks 1 through 3) and about 26% low molecular weight species (Peak 4 and 5) and a Peak 4 to Peak 3 ratio of about 0.1. The HPLC of this material is shown in FIG. 1A. (For the sake of comparison, FIG. 2 is the HPLC taken from the literature of a non-enhanced aluminum antiperspirant salt of similar composition.)

Table 1 Example 2 shows the composition of the same material after heating a dilute (8% salt solution) at 100° C. for two hours. As expected, high molecular weight Peaks 1 through Peak 3 materials are diminished and low molecular weight Peak 4 materials are enhanced. In this example, the solution contains about 74% of the low molecular weight species in Peak 4, about 83% of Peak 4 & 5 and a Peak 4 to Peak 3 ratio of greater than 4.0. The HPLC of this material is shown in FIG. 1B. (For the sake of comparison, FIG. 3 is the HPLC taken from the literature of an aluminum-zirconium antiperspirant salt with Peak 4 to Peak 3 ratio of greater than about 1.3.)

In summary, Group 1 Materials are prepared through a multi-step process that requires manufacturing high basicity PAC from aluminum metal. Many of the references cited herein teach the use of aluminum powder which is more expensive than other sources of aluminum metal. The high basicity PAC prepared in the first step is then enhanced by diluting it to a 10% salt or less concentration and heating it for several hours at about 100° C. If an enhanced aluminum-zirconium antiperspirant salt is being prepared the zirconium component is added either before or after the heat treating process. The dilute solution of enhanced efficacy antiperspirant salt is then rapidly spray dried in order to obtain the enhanced efficacy antiperspirant salt. Said antiperspirant salt is then formulated into consumer products.

One undesirable attribute of Group 1 Materials is their lack of stability in aqueous solution. These materials must be rapidly dried in order to preserve the increased low molecular weight, Peak 4 content. In the absence of rapid drying, the materials rapidly revert back to their high molecular weight counterparts. Upon drying, Group 1 Materials are formulated into costly non-aqueous compositions which require expensive carriers (e.g. cyclomethicone) in order to maintain the characteristic of increased sweat inhibition.

Group 2 Materials provide increased sweat inhibition and have the added benefit of being stable in aqueous solution for extended periods. (See U.S. Pat. No. 6,902,724 (Parekh), U.S. Pat. No. 6,649,152 (Carrillo) and U.S. Pat. No. 6,991,780 (Carrillo) and references contained therein.) The stability attribute provides for cost savings in manufacturing antiperspirants by eliminating the need for rapid drying, and or permitting the substitution of water for expensive carriers.

The procedure for manufacturing Group 2 Materials requires preparation of high basicity PAC from aluminum metal. Again expensive aluminum powder is recommended for this purpose. High basicity PAC is then enhanced by heating a dilute solution to about 100° C. for several hours. Zirconium components are added either prior to or after the heating process. U.S. Pat. No. 6,649,152 teaches that the aluminum-zirconium salt with high Peak 5 content is preferably spray dried in order to obtain a salt with maximum efficacy. Thus, the procedures for manufacturing Group 2 Materials offer little improvement over the processes for manufacturing Group 1 Materials.

Group 2 Materials are stable over time due to their high Peak 5 composition. Table 1 Example 3 shows the composition of a Group 2 material composed of aluminum and zirconium. The amount of Peak 5 material required to impart stability in aqueous solution is dependent on several factors. In the case of aluminum antiperspirant salts, U.S. Pat. No. 6,902,724 teaches that this stability is imparted when Peak 5 ranges from 15% to 50% and the Peak 4 plus Peak 5 composition is at least 45% and no more than 70%. The report further teaches that the Peak 4 to Peak 3 ratio is unimportant. Although low molecular weight Peak 4 and Peak 5 components are known to provide increased sweat inhibition by blocking pores more effectively than their high molecular weight counterparts, this report teaches away from compositions containing more than 50% Peak 5 and more than 70% Peak 4 plus Peak 5. No examples or explanation is offered with regard to this omission in the teachings.

In the case of aluminum-zirconium antiperspirant salts, U.S. Pat. No. 6,649,152 teaches that stability is imparted when the Peak 5 composition is at least 45%, the Peak 4 to Peak 3 content is typically 20% to about 50%, the Peak 4 to Peak 3 ratio is at least 0.4 and substantially all of the aluminum is found in Peaks 3, 4 and 5. (This set of criteria can be shown to be mathematically equivalent to the criteria shown in Table 2 for Group 2 Materials comprised of aluminum and zirconium.) An aluminum-zirconium antiperspirant salt meeting the requirements of Group 2 Materials is shown in Example 3 of Table 1. In this example the material contains 72% Peak 5, an estimated Peak 4 plus Peak 5 content of 87% and a Peak 4 to Peak 3 ratio of 1.1. The HPLC of this Group 2 Material is shown in FIG. 4. Thus, U.S. Pat. No. 6,649,152 and a related U.S. Pat. No. 6,991,780 which are directed toward Group 2 Material comprised of aluminum-zirconium combinations, teach the benefit of high Peak 5 content with a Peak 4 to Peak 3 ratio of at least 0.4, however their teachings do not address Group 2 Materials of aluminum and zirconium exclusively composed of Peak 5.

Criteria for defining Group 1 Materials and Group 2 Materials based on generally recognized definitions by skilled artisans are summarized below in Table 2.

TABLE 1

| Example | Sample Description | Basicity | Peak 5 Area | Peak 4 Area | Peak 3 + 2 + 1 Area | Peak 4 to Peak 3 Ratio | Peak 4 + Peak 5 Area | |
|---|---|---|---|---|---|---|---|---|
| 1 | Non-enhanced Material | 83% | 16% | 9% | 74% | 0.13 | 26% | FIG. 1A |
| 2 | Group 1 Material | 83% | 8% | 75% | 17% | 4.39 | 83% | FIG. 1B |
| 3 | Group 2 Material | 66% | 72% | 15% | 14% | 1.1 | 87% | FIG. 4 |

TABLE 2

| | Al Antiperspirant Compositions | Al—Zr Antiperspirant Compositions |
|---|---|---|
| Group 1 Materials: | Peak 4:Peak3 Ratio >0.5 | Peak 4:Peak3 Ratio >0.5 |
| Group 2 Materials: | Peak 5 of 15% to 50% | Peak 5 >45% |
| | Peak 4:Peak3 Ratio unimportant | Peak 4:Peak3 Ratio >0.4 |
| | Peak 4 + Peak 5 of 45%–70% | Peak 4 + Peak 5 >60% |

In summary, the efficacy of aluminum and aluminum-zirconium antiperspirants is determined by the amount of low molecular weight Peak 4 and Peak 5 components present. Superior efficacy is obtained when the high molecular weight materials in Peaks 1, 2 and 3 are minimized. When this goal is accomplished by maximizing Peak 4, enhanced efficacy is obtained but the material is unstable in aqueous solution. When this goal is accomplished by maximizing Peak 5, enhanced efficacy and stability in aqueous solution is obtained.

A need therefore exists that overcomes one or more of the above identified issues.

BRIEF DESCRIPTION OF THE DRAWINGS

FIG. 4 is a HPLC analysis of 40% basic PAC.

SUMMARY OF THE INVENTION

Figure 1A:
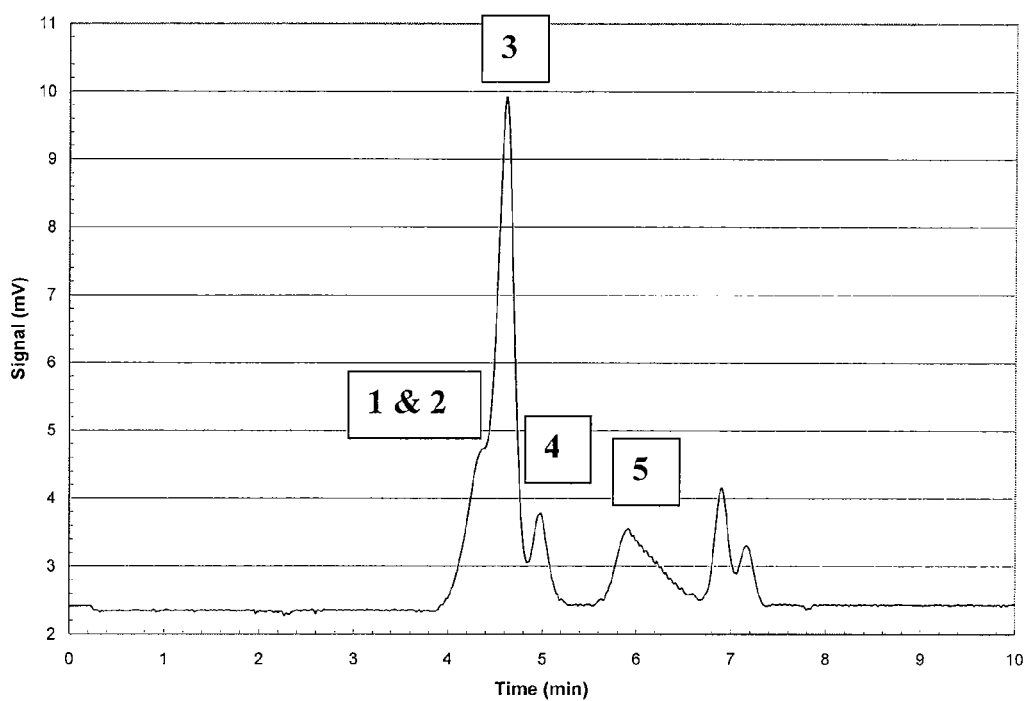
FIG. 1A is a HPLC analysis of conventional (non-enhanced) ACH.

The present invention embraces processes for increasing the basicity of aluminum and aluminum-zirconium compounds.

Surprisingly these processes produce low molecular weight species which are known to provide enhanced efficacy characteristics in antiperspirant applications. The present processes are unique when compared to existing commercial processes for making said products insofar as they do not require aluminum metal as a raw material. Eliminating aluminum metal as a raw material for producing aluminum antiperspirant salts and aluminum-zirconium antiperspirants salts provides a solution to a long felt unmet need. The processes can produce products of a wide range of basicities and are particularly useful in producing high basicity products. The processes of the present invention produce a wide range of solution concentrations. The processes of the present invention produce high purity products. The processes described herein can also be utilized to produce enhanced efficacy aluminum and enhanced efficacy aluminum-zirconium compounds in high concentration. The processes of the present invention produce enhanced efficacy aluminum antiperspirant salts and enhanced efficacy aluminum-zirconium antiperspirant salts in a more straight forward manner than the process currently utilized by industry.

In one aspect, the present invention provides processes for producing aluminum and aluminum-zirconium antiperspirant salt compositions that do not require the use of aluminum metal.

In another aspect, the present invention provides methods for producing Group 1 Materials and Group 2 Materials where costly raw materials and processing steps are reduced or eliminated.

In still another aspect, the present invention provides Group 2 antiperspirant salt compositions.

DETAILED DESCRIPTION OF THE INVENTION

The present invention embraces processes for increasing the basicity of aluminum and aluminum-zirconium compounds.

Surprisingly these processes produce low molecular weight species which are known to provide enhanced efficacy characteristics in antiperspirant applications. The present processes are unique when compared to existing commercial processes for making said products insofar as they do not require aluminum metal as a raw material. Eliminating aluminum metal as a raw material for producing aluminum antiperspirant salts and aluminum-zirconium antiperspirants salts provides a solution to a long felt unmet need. The processes can produce products of a wide range of basicities and are particularly useful in producing high basicity products. The processes of the present invention produce a wide range of solution concentrations. The processes of the present invention produce high purity products. The processes described herein can also be utilized to produce enhanced efficacy aluminum and enhanced efficacy aluminum-zirconium compounds in high concentration. The processes of the present invention produce enhanced efficacy aluminum antiperspirant salts and enhanced efficacy aluminum-zirconium antiperspirant salts in a more straight forward manner than the process currently utilized by industry.

The products of the present invention are compounds of Formula I:

$$M_m(OH)_n X_{am-n} \tag{I}$$

wherein "a" is the valence of the metal ion;
X is an anion;
0<n≤am; and
m≥1.

The present invention surprisingly provides processes that increase the hydroxide content (i.e., the basicity) of compounds having the Formula I, wherein M is a metal (or combination of metals) that undergoes the reaction below. Examples of such metals include but are not limited to aluminum, zirconium, titanium and iron.

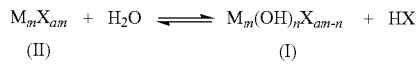

$$M_mX_{am} + H_2O \rightleftharpoons M_m(OH)_nX_{am-n} + HX$$
$$(II) \qquad\qquad\qquad (I)$$

The increase in hydroxide content (i.e., basicity) is accomplished by subjecting an aqueous solution of Compound I to electrodialysis, such that the HX concentration in the solution is decreased. Therefore, HX is effectively removed from the solution and from Compound I, thereby providing Compound I with increased hydroxide content relative to Compound I prior to electrodialysis treatment.

Alternatively, or in combination with the electrodialysis treatment of Compound I, Compound II can be subjected to conditions that cause Compound II to undergo a transformation to form Compound I with generation of HX. Again, during the electrodialysis treatment, HX is removed from solution, thereby providing Compound I with an increased hydroxide (increased basicity) content.

In particular, M can be aluminum (Al), titanium (Ti), zirconium (Zr), or iron (Fe). X can be nitrate or a halide such as chloride, bromide, or iodide.

When M is aluminum, the aforementioned processes produce products with basicities ranging from ~1% to ~85%. Because, higher basicity products generally have greater utility, the processes preferably produce products of basicity greater than 50%, more preferably the processes produce products of basicity greater than 60%, and most preferably the process produces products of basicity greater than 65%. One particular interest is the use of these processes to produce aluminum chlorohydrate with a basicity of about 83% (in this case, X is Cl in the above formula and the aluminum to chloride ratio is from about 1.91:1 to about 2.10:1 with corresponding basicities of 82.5% to 84.2%).

In another embodiment, a mixture of Compounds I and/or II with different metals (M), are subjected to the electrodialysis. For example, when aluminum and zirconium compounds of formula I and/or II are subjected to the electrodialysis treatment, aluminum-zirconium complexes with increased basicity are produced. Although the present invention can be used to produce aluminum and aluminum-zirconium compounds with a wide range of basicities, of particular relevance is the ability to produce antiperspirant salt compositions as defined by the Official Monographs of the United States Pharmacopeia (U.S.P.). Thus, a preferred aluminum antiperspirant salt compositions salt taught by the present invention is ACH, a basic aluminum chloride with aluminum to chloride ratio between about 1.9:1 to about 2.1:1 or aluminum sesquichlorohydrate, a basic aluminum chloride with aluminum to chloride ratio of about 1.26 to about 1.90. A preferred aluminum zirconium antiperspirant salt compositions salt taught by the present invention is an aluminum zirconium chlorohydrate, more preferably an aluminum zirconium tetrachlorohydrate (Al:Zr=about 2 to about 6; M:Cl=about 0.9 to about 1.5) or aluminum zirconium octachlorohydrate (Al:Zr=about 6 to about 10; M:Cl=about 0.9 to about 1.5) or aluminum zirconium pentachlorohydrate (Al:Zr=about 6 to about 10; M:Cl=about 2.1 to about 1.5) or aluminum zirconium trichlorohydrate (Al:Zr=about 2.0 to about 5.99; M:Cl=about 2.1 to about 1.5). M:Cl is defined by the U.S.P. as the total metal (Al⁺ Zr) to chloride ratio.

Preferred aluminum salts for use as starting materials are those having the empirical formula $Al_2(OH)_nX_{6-n}$ wherein X is Cl, Br, I, or $NO_3$, preferably Cl; and n is about 0 to 5. The processes of the present invention are applicable to materials wherein n ranges from about 0 to about 5, however materials defined by n ranging from 0 to 3 are of particular interest due to their availability from economical routes. The aluminum salts also generally have some water of hydration associated with them Preferred zirconium salts for use as starting materials are those having the general formula $Zr(OH)_{4-b}X_b$ wherein X is Cl, Br, I, or $NO_3$, preferably Cl; and b is about 0.7 to about 4.0. Although written for convenience as $Zr(OH)_{4-b}X_b$ this salt is intended to include zirconium oxychloride and zirconium hydroxychloride, which is also often written as $ZrO(OH)_{2-b}Cl_b$ (where b in this instance, is about 1 to about 2). The term zirconium hydroxyl-chloride is used herein to refer to compounds of the formula $Zr(OH)_{4-b}Cl_b$ where b=about 0.7 to about 4.0 throughout this text. The zirconium salts also generally have some water of hydration associated with them, typically about 1 to about 8 moles per mole of salt. As an alternative to or in conjunction with the above described aluminum and zirconium salts, it is also possible to employ zirconium basic carbonate $(Zr_2(OH)_4(CO)_3.nH_2O)$ as a starting material.

Zirconium salts with a low Zr:X ratio are useful because such salts tend to have a lower molecular weight than other zirconium salts. It is theorized that the use of low molecular weight zirconium salts results in higher antiperspirant efficacy in the final aluminum-zirconium salt. Because the processes of the present invention are designed for increasing basicity by extracting acids of the formula HX, said processes are well suited for accomplishing this goal. And because the processes of the present invention can be operated under mild conditions, in particular at low temperature when compared to other processes, formation of undesirable high molecular weight zirconium species is minimized.

Addition of an amino acid can help to stabilize aluminum and aluminum-zirconium complexes. The amino acid may be added either before, during or after the electrodialysis process. Therefore, one family of aluminum and aluminum-zirconium compounds advantageously produced by the present invention is defined by the formulas:

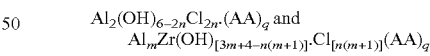

$$Al_2(OH)_{6-2n}Cl_{2n}\cdot(AA)_q \text{ and}$$
$$Al_mZr(OH)_{[3m+4-n(m+1)]}\cdot Cl_{[n(m+1)]}(AA)_q$$

where m is between about 2.0 and about 10.0, in particular between about 3.0 and about 8.0;
where n is between about 0.48 and about 1.11, which corresponds to a metal (Al+Zr) to anion (e.g., Cl⁻) ratio of M:X equal to between about 2.1 and about 0.9; q is between about 0 and about 4.0, and AA is an amino acid such as glycine, alanine, valine, serine, leucine, or aminobutyric acid. Suitable other amino acids and salts of other amino acids that may be used in the present invention will be evident to those skilled in the art. In addition to amino acids per se, such as glycine, amino acid compounds that are useful herein include alkali metal salts and alkaline earth metal salts of amino acids as well as ammonium salts of amino acids. The alkali metal salts and alkali earth metal salts may be introduced into the antiperspirant salt composition in their final form or they maybe generated in situ. The amino acid and amino acid salts may be incorporated into the antiperspirant salt composition prior to, during or after the electrodialysis process.

The aluminum and aluminum-zirconium antiperspirant salts of the present invention can be combined with organic solvents such as polyhydric alcohols in order to improve their solubility in certain formulations (e.g., clear stick gels) without sacrificing antiperspirant efficacy. The polyhydric alcohol will typically have from three to six carbon atoms and from two to six hydroxyl groups. Polyhydric alcohols commonly employed include but are not limited to propylene glycol, glycerin and polyethylene glycol. Alternatively, organic solvents having at least two carbon atoms and at least one hydroxyl group may be used; said organic solvents include but are not limited to ethanol, propanol, iso-propanol, and butanol. The organic solvents may also be combined with aluminum antiperspirant salt compositions and aluminum zirconium antiperspirant salt compositions that contain amino acids. The addition of organic solvents may be prior to, during or after the electrodialysis process.

Calcium ions are known to stabilize polyaluminum chloride compositions. Said calcium ions may be introduced to the antiperspirant salt compositions of the present invention by adding a variety of calcium salts. The calcium salts include calcium hydroxide, calcium carbonate and calcium chloride and they may be added in quantities from 0 to 2%. The addition of calcium salts may be prior to, during or after the electrodialysis process.

The products of the present invention may be used or stored as an aqueous solution or they may be spray dried or vacuum dried to obtain the antiperspirant salt compositions in solid powder form.

The present invention surprisingly provides the ability to prepare enhanced efficacy aluminum and aluminum-zirconium compounds in essentially a single step. Heretofore, enhanced efficacy aluminum and aluminum-zirconium compounds were prepared through multi-step processes that were dependent on the conventional oxidation of aluminum metal with hydrochloric acid.

Electrodialysis is an electrochemical process in which ions are transported through ion permeable membranes from one solution to another under the influence of a potential gradient. The electrical charges on the ions allow them to be driven through the membranes fabricated from ion exchange polymers. Applying a voltage between two end electrodes generates the potential field required for ion transport across membranes to occur. Since the membranes used in electrodialysis have the ability to selectively transport ions having positive or negative charge and reject ions of the opposite charge, useful concentration, removal, or separation of electrolytes can be achieved by electrodialysis.

Commercial applications of electrodialysis include:
The removal of salt from brackish water to generate drinking water.
The concentration of salt from seawater up to 20% salt content, as a first step toward salt manufacture.
The reduction of minerals from whey to manufacture infant formula.
And the reduction of the salt content in soy sauce.

Figure 5:
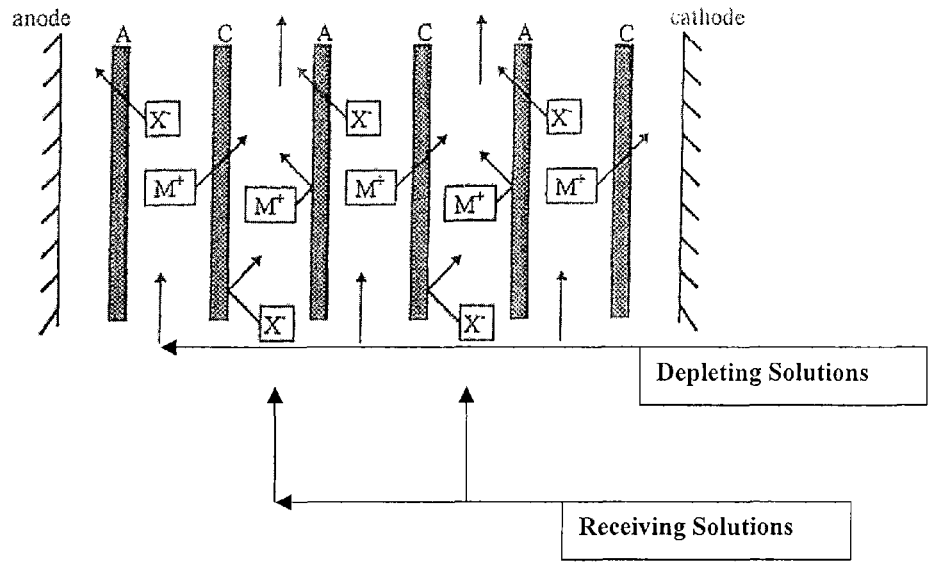
FIG. 5 depicts an electrodialysis stack and demonstrates the removal of electrolyte, MX from depleting solution and the concentration of MX in the receiving solution.

The device used for electrodialysis processes is generally referred to as an electrodialysis stack. The essential elements of an electrodialysis stack are an anode, a cathode, cation permeable membranes and anion permeable membranes. FIG. 5 is a depiction illustrating the basic components and operation of an electrodialysis process. Thus, the cation and anion permeable membranes are placed between the anode and the cathode in alternating fashion. Assembling the ion permeable membranes in this fashion creates two distinct sets of compartments. The first set of compartments or cells is comprised of an anion permeable membrane on the anode side and a cation ion permeable membrane on the cathode side. This set of cells is oriented with respect to the anode and the cathode so that electrolytes are depleted from these cells when a voltage is applied. The solutions in this set of compartments are referred to as the depleting stream. The second set of compartments or cells is comprised of an anion permeable membrane on the cathode side and a cation permeable membrane on the anode side. This set of cells is oriented with respect to the anode and the cathode so that electrolytes are received and concentrated in these cells when a voltage is applied to the electrodes. The solutions in this second set of compartments are referred to as the receiving or the enriching stream. Thus, the net effect of the electrodialysis process is to transfer electrolytes from the depleting solution to the receiving solution where said electrolytes are concentrated.

Successful application of electrodialysis requires that the process under consideration has the ability to support a high rate of ion transfer across the ion permeable membrane surfaces for extended periods. The rate of ion transfer across membrane surfaces is referred to as the ionic flux and is measured in mole/sec-cm$^2$. The ionic flux is related to the electrical charge passed through the electrodialysis cell by the following relationship:

$$\text{Ionic Flux} = \frac{\text{Current Density (coulombs/sec} - \text{meter}^2)}{\text{Faraday's Constant (96,485 coulombs/mole)}}$$

Since coulombs/sec is equivalent to amperes, the current density (C.D.) is commonly measured in mamp/cm$^2$. Successful electrodialysis processes (utilizing hydrocarbon membranes configured as described above) generally support a C.D. from ~10 to ~50 mamp/cm$^2$. Current densities below ~10 mamp/cm$^2$ are generally impractical due to the large amount of ion permeable membrane required and current densities above ~50 mamp/cm$^2$ are generally impractical due to physical limitations of the ion permeable membranes.

Figure 6:
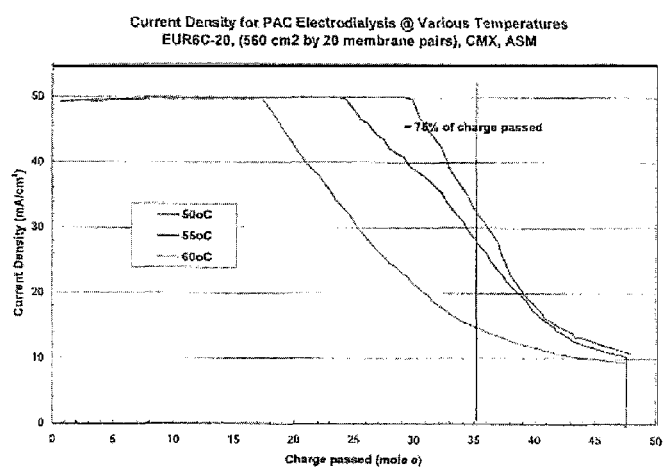
FIG. 6 shows the current density as a function of basicity at 50° C., 55° C. and 60° C. and demonstrates the benefit of operating the electrodialysis processes of the present invention at elevated temperatures.

Electrodialysis processes are commonly performed at ambient temperatures; the commercial processes mentioned above are all performed at ambient temperatures. It was surprisingly found that current densities for the processes of the present invention are markedly improved by operating at increased temperature. FIG. 6 compares the current density at 50° C., 55° C. and 60° C. as a function of basicity for the electrodialysis processes of the present invention. The information depicted in this diagram shows that current density is reduced as the basicity is increased but that the reduction in current density is mitigated by increasing temperature. This reduction in current density at increased basicity was confirmed by operating the electrodialysis processes of the present invention at various temperatures. Operation at 55° C. to 65° C. permitted current densities of 50 to 40 mamp/cm$^2$ to be realized over the range of basicities from about 40% to about 70%; in contradistinction operation at ambient temperature resulted in current densities of 42 to 18 mamp/cm$^2$ over the same range of basicities. At 55° C. the current density at 83% basicity was 30 mamp/cm$^2$; while operation at ambient temperature resulted in a current density of 2-4 mamp/cm$^2$ at 83% basicity. Without being bound by theory, these observations suggest that polyaluminum chlorides participate in a process that causes membrane fouling as the basicity increases and that this fouling process is mitigated as the temperature is increased.

The observations cited above demonstrate that the current density for the electrodialysis processes of the present invention increases as the temperature of operation increases. The temperature of operation for electrodialysis is limited by various characteristics related to the materials of construction of the electrodialysis stack. Although, ion permeable hydrocarbon membranes rated to 80° C. of operation are available, operation above 40° C. is uncommon. Stack distortion, spacer manufacturing technology and spacer integrity are the primary factors limiting higher temperature operation. Stack components that permit the present invention to operate at temperatures up to 65° C. were utilized in the present work. Operation at temperatures higher than 65° C., while not practical with components currently available would be beneficial to the process of the present invention.

Membrane fouling, the deposition of materials (e.g., solids and or gels) that inhibit ion permeable membrane performance, leads to membrane degradation and must be minimized in order to maintain high current densities for extended periods. Macromolecules with ionizable functionalities promote membrane fouling since their charge causes them to migrate to the ion permeable membrane surface but their size prevents passage through said membrane. Polyaluminum chloride solutions form macromolecules and this attribute adversely influences the performance of electrodialysis. The propensity of PAC solutions to form macromolecules increases as the basicity increases and or as the concentration of the PAC solution increases. At basicities of greater than about 50% and or concentrations above about 1 molar (measured on an aluminum basis) membrane fouling adversely impacts the processes of the present invention. It was surprisingly found that fouling can be minimized by either using freshly prepared starting materials and or heat treating the reaction solutions prior to or during the electrodialysis process. It was surprisingly discovered, that feed stocks for the electrodialysis processes of the present invention perform best if they are less than 30 days old, preferably less than 20 days old, and most preferably used within 10 days from the time they are manufactured. The heat treating process of the present invention is conveniently performed by heating the feed solutions to a temperature of 70° C. to boiling for a period of 15 min to 24 hours. The heat treating procedure of the present invention is carried out expediently by heating the feed solutions to a temperature of 90° C. for a period of one hour.

Successful application of electrodialysis also requires that the ion permeable membranes have a high degree of selectivity with respect to ion transport. Current efficiency is a measure of the selectivity of ion transport. The current efficiency is the ratio of current used by the desired process (removal of $H^+$ and mono-valent anion (e.g., $Cl^-$) in the present invention) to the total current consumed by ion transport. Low current efficiencies indicate the presence of nonselective ion transport. High current efficiencies are important to the economics of electrodialysis since the current efficiency impacts the size of the electrodialysis cell, the electrical power consumed and product purity.

While back migration of anions across cation permeable membranes is uncommon, back migration of $H^+$ across anion permeable membranes is common in acidic media. The processes of the present invention operate under acidic conditions (pH<3.5) and back migration of $H^+$ across anion membrane is ideally minimized in order to maintain high current efficiency. In addition, the processes of the present invention require that $H^+$ (present in concentrations of ~$10^{-1}$ molar to ~$10^{-3}$ molar) in the depleting solution be transferred across the cation permeable membranes in preference to metal cations like $Al^{-3}$ and $Zr^{+4}$ (present in concentrations of greater than about 1 molar when measured on an metal basis). Nonselective cation transport can lead to reduced current efficiency and contamination of the depleting and or the receiving solution.

It was surprisingly discovered that highly selective ion transport (i.e., minimum back migration of $H^+$ across anion permeable membrane and minimum contamination of the depleting solution) and high current efficiencies (greater than 85%-90%) result from appropriate selection of the receiving solution employed. When polyaluminum chloride with basicity greater than ~5%, preferably basicity greater than ~10% is used as the receiving solution, the hydrochloric acid removed from the depleting solution reacts with the PAC in the receiving solution. Thus, utilizing PAC as the receiving solution maintains the hydrochloric acid concentration in the receiving solution at low levels, back migration of hydrogen ion is markedly reduced and high current efficiencies are realized.

In comparison, when PAC is replaced by aluminum chloride as the receiving solution, the solution becomes rich in hydrochloric acid and the current efficiency drops to impractical levels (<63%). The use of calcium chloride with calcium hydroxide as the receiving solution was also examined. The calcium chloride-hydroxide receiving solution gave current efficiencies of about 60% to 80%.

The overall process for the all aluminum system (i.e., when M=Al) is characterized by the reaction sequence below:

Depleting Solution:

$$Al_2(OH)_{6-x}Cl_x + H_2O \longrightarrow Al_2(OH)_{6-(x-1)}Cl_{x-1} + HCl$$

Figure 7:
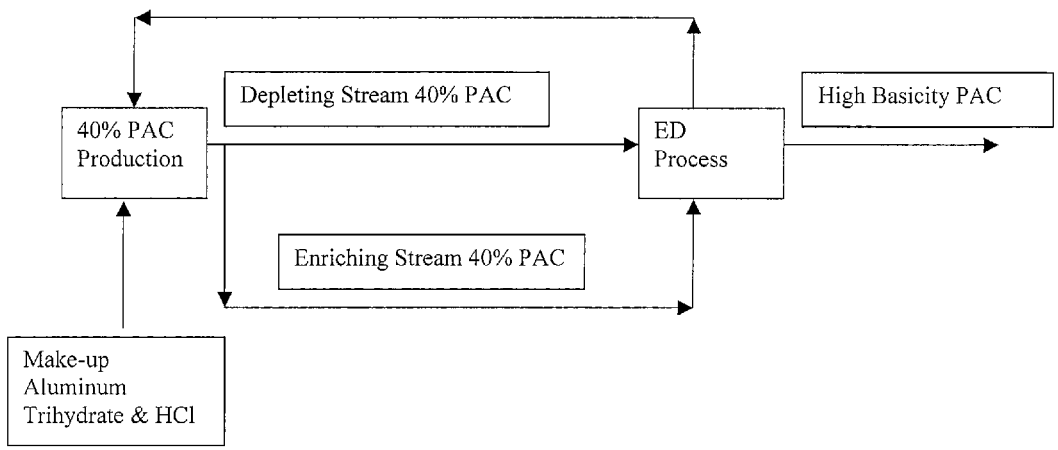
FIG. 7 is a schematic representation which depicts one mode of operation for the over all process. In this schematic the receiving solution and the depleting solution are both comprised of polyaluminum chloride solutions. The depleting solution becomes more basic and the receiving solution becomes less basic due to the electrodialysis process.

Receiving Solution:

$$Al_2(OH)_{6-y}Cl_y + HCl \longrightarrow Al_2(OH)_{6-(y+1)}Cl_{y+1} + H_2O$$

wherein x varies from about 2 to about 6, y varies from about 1 to about 5, and whereby the HCl present in the PAC solution of the depleting compartments is transferred across the ion permeable membranes to the receiving solution. The HCl so transferred across ion permeable membranes reacts with the PAC present in the receiving solution. The overall process causes the PAC in the depleting solution to become more basic (due to the current driven removal of HCl) and the PAC in the receiving solution to become less basic. The PAC of the receiving solution is utilized in the manufacturing process as depicted in FIG. 7 wherein said PAC is removed from the electrodialysis process and its basicity is increased by reaction with aluminum trihydrate ($Al_2O_3 \cdot 3H_2O$). Thus, the overall process is highly efficient with respect to raw materials because the hydrochloric acid removed from the depleting solution is used to manufacture more additional) PAC (see FIG. 7).

The basicities of the PAC solutions in the reactions above and in FIG. 7 are used for illustrative purposes and other combinations of practical basicities will be readily apparent to those skilled in the art. And although the depleting stream in the example above and in FIG. 7 is represented as $Al_2(OH)_{6-x}Cl_x$, the depleting stream can be any composition of Formula I or Formula II:

$$M_m(OH)_nX_{am-n} \quad (I)$$

wherein "a" is the valence of the metal ion;
X is an anion;
0<n≤am; and
m≥1.
which undergoes the reaction below.

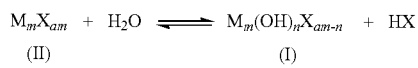

Most electrodialysis processes are based on the use of monolayer membranes made from functionalized organic moieties like divinylbenzene and styrene. These membranes are commonly referred to as hydrocarbon membranes in order to differentiate them from membranes made from functionalized polytetrafluoroethylenes (PTFE). The hydrocarbon membranes are inexpensive when compared to their PTFE counterparts and their use is preferred in mild applications (i.e., near neutral pH, ambient temperature, and the absence of redox processes). Hydrocarbon membranes are available as both anion permeable membranes and cation permeable membranes; while PTFE membranes are primarily available as cation permeable membranes. Interestingly, these two types of membranes have distinctly different physical structures and modes of operation. While the hydrocarbon membranes are considered to function as continuous gels, the PTFE membranes are thought to be composed of a rigid hydrophobic backbone structure filled with hydrophilic channels where ion transport takes place. While physical evidence supports the idea that hydrocarbon and PTFE membranes operate through different mechanisms, both function to provide highly effective ion transport. The processes of the present invention can be practiced with either hydrocarbon membranes or PTFE membranes.

The processes of the present invention are operated in either a batch, semi-continuous mode (commonly referred to as the "shallow dump" process) or a continuous mode (commonly referred to as the "feed and bleed" process). Shallow dump refers to a mode of operation whereby after the electrodialysis process is taken to completion, the depleting and receiving solutions are partially drained from their respective recycle loops. The recycle loops are then replenished with fresh starting solutions and the electrodialysis process is repeated. Feed and bleed refers to a mode of operation whereby the electrodialysis process is maintained in a steady state; finished product is continuously bled from the recycle loop and replenished with starting material. All three modes of operation accommodate the opportunity to practice an operation known as CIP (cleaning in place) whereby the electrodialysis process is discontinued, receiving solutions and depleting solutions are removed from the electrodialysis stack and membranes are washed with a cleaning solution. Although any number of cleaning solutions may be utilized, the processes of the present invention are particularly responsive to acidic cleaning solutions; preferably hydrochloric acid cleaning solutions.

Figure 1B:
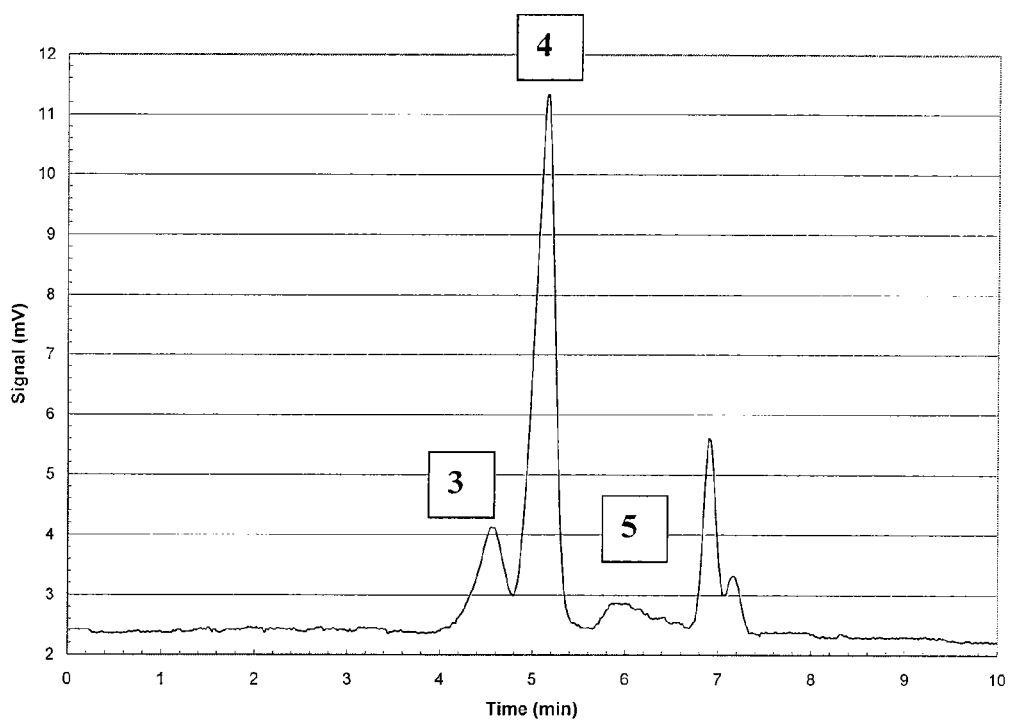
FIG. 1B is a HPLC analysis of a sample of enhanced-efficacy ACH wherein the Peak 4 to Peak 3 ratio is greater than 0.5.
Figure 2:
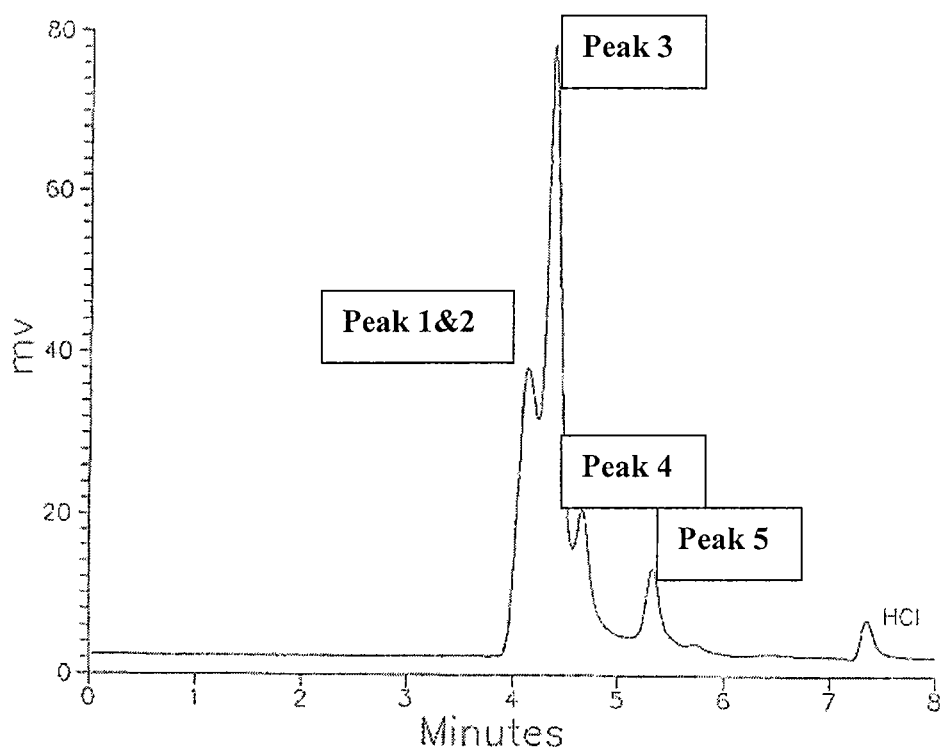
FIG. 2 is a HPLC analysis of conventional (non-enhanced) ACH taken from the literature.
Figure 3:
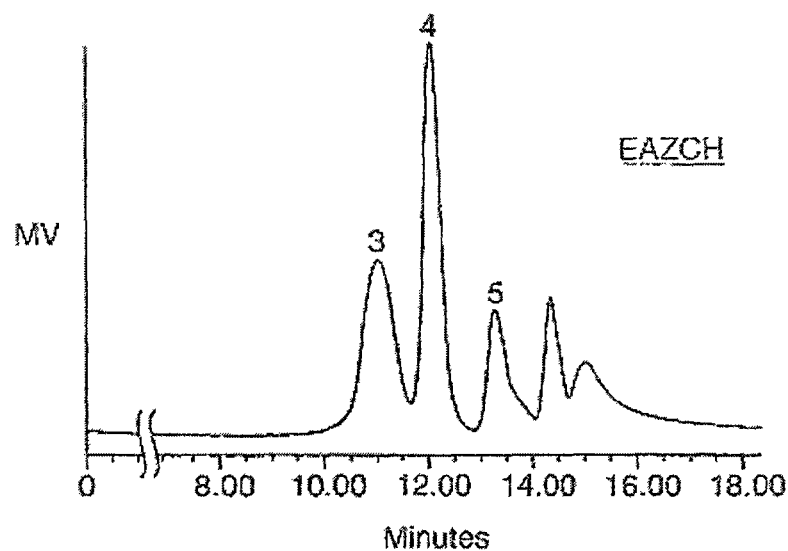
FIG. 3 is a HPLC analysis of a Group 1 Material. In this instance it is a Group 1 Material; an enhanced efficacy aluminum-zirconium tetrachlorohydrate-glycine antiperspirant salt with Peak 4 to Peak 3 content of about 1.3.
Figure 4:
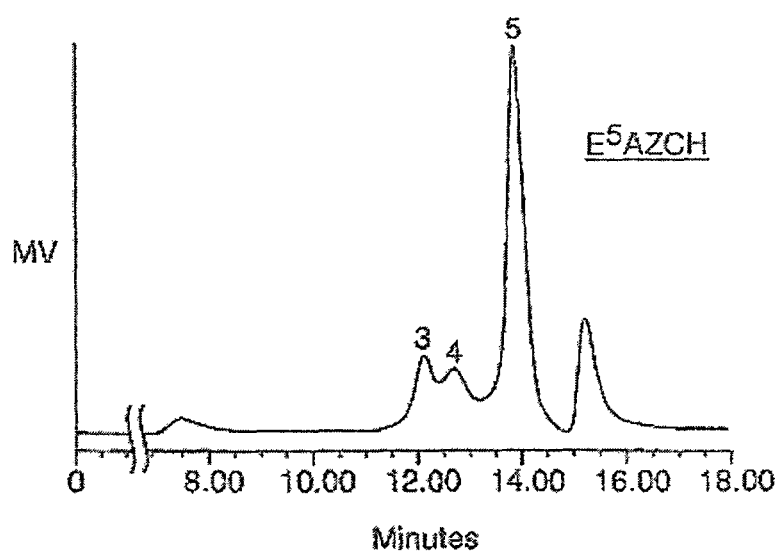
FIG. 4 is a HPLC analysis of Group 2 Material. In this instance it is an enhanced efficacy aluminum-zirconium octachlorohydrate-glycine antiperspirant salt that contains 72% Peak 5, an estimated Peak 4 plus Peak 5 content of 87% and a Peak 4 to Peak 3 ratio of 1.1.

As previously discussed, ACH is an important intermediate for the preparation of enhanced efficacy antiperspirant salts. ACH is produced commercially by the reaction of expensive aluminum powder with hydrochloric acid. Table 1 and FIG. 1 demonstrate that ACH produced by this route is primarily high molecular weight Peak 1, Peak 2 and Peak 3 materials.

Figure 8:
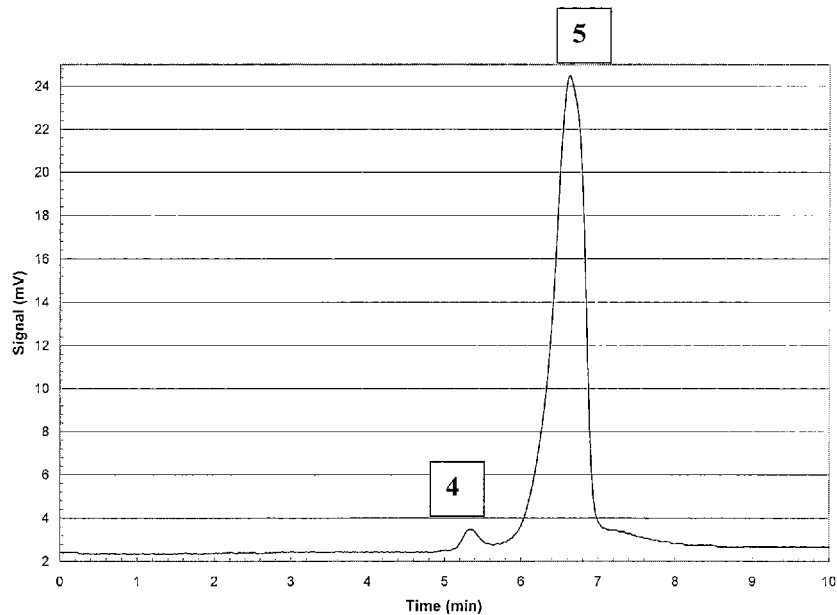
FIG. 8 is a HPLC analysis of 40% basic PAC.

Low basicity PAC is known to be comprised of low molecular weight materials. FIG. 8 shows the HPLC analysis of 40% PAC and demonstrates that this material is composed exclusively of Peak 4 materials (2%) and Peak 5 materials (98%); there is no Peak 1 through Peak 3 materials.

When 40% PAC is subjected to electrodialysis under the conditions taught by the present invention the basicity is increased. It was surprisingly discovered that as the electrodialysis process proceeds and the basicity increases that high proportions of Peak 4 and Peak 5 components are retained even at high basicities commonly used in antiperspirant salt compositions. Table 3 shows the composition of samples taken from the electrodialysis process as the reaction proceeds. The electrodialysis process for the Table 3 examples was conducted at 65° C.

Figure 9:
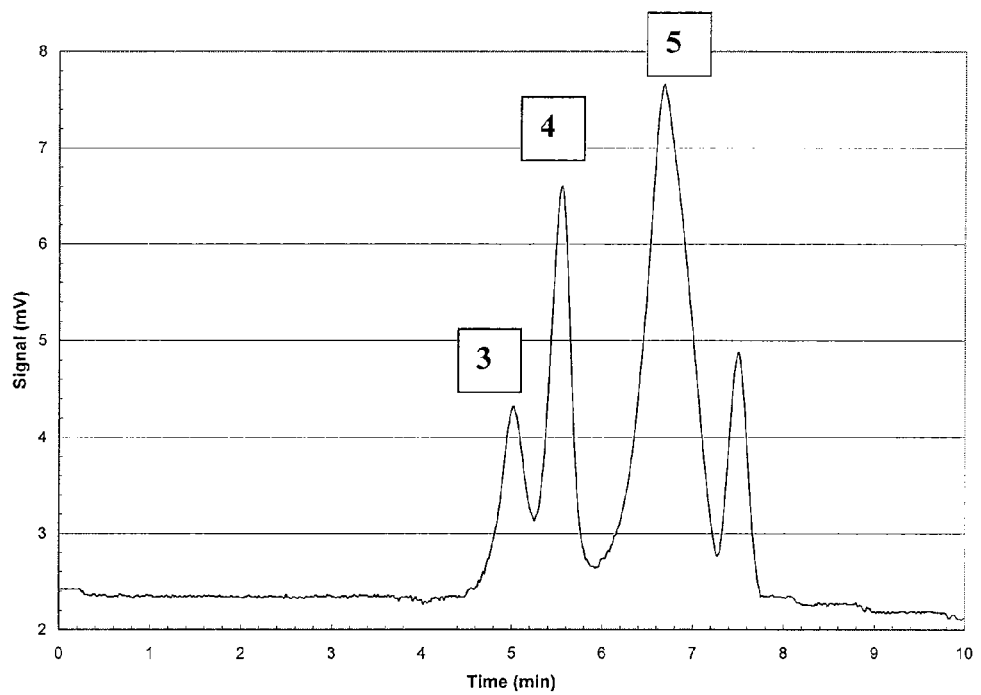
FIG. 9A is a HPLC analysis of an enhanced efficacy 72% basic PAC of the present invention.
FIG. 9B is a HPLC analysis of an enhanced efficacy 72% basic PAC of the present invention after ageing for 2 months.
Figure 9:
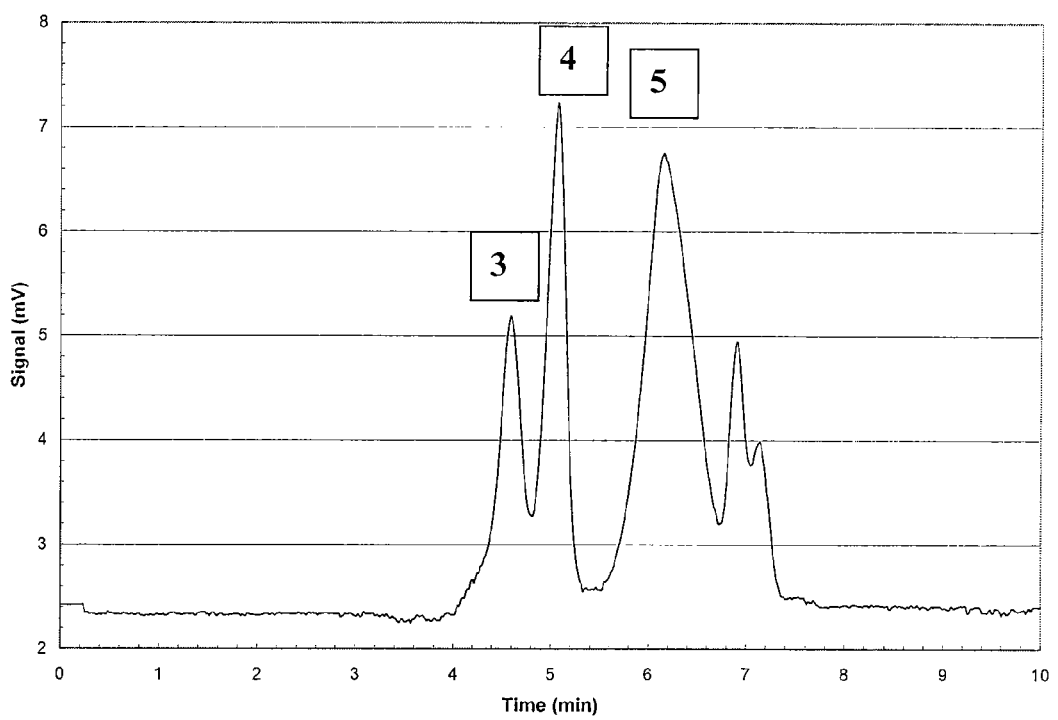

The results in Table 3 indicate that Peak 5 composition exceeds 50% and that the Peak 4 plus Peak 5 composition exceeds well over 70% up to 75% basicity. Example 8 in Table 3 demonstrates the products of the present invention are stable over time, retaining a Peak 5 composition exceeding 50% and a Peak 4 plus Peak 5 composition exceeding 70%. The point is further confirmed by FIGS. 9A and 9B which show the HPLC analysis of freshly prepared 72% PAC prepared by the processes of the present invention (FIG. 9A) and an HPLC analysis of the same sample analyzed two months later (FIG. 9B). Thus, electrodialysis of low basicity PAC under the conditions of the present invention produces Group 2 Materials with unique composition up to ~75% basicity (see Examples 1-6). And, at basicities of greater than 75%, Group 2 Materials are produced (see Example 7). Table 3 also shows that the Peak 4 to Peak 3 ratio exceeded 1.0 in all cases.

An additional benefit of the processes of the present invention is the relatively high concentration of products produced. The $Al_2O_3$ concentration of Example 5 in Table 3 is 15.5%. This $Al_2O_3$ concentration corresponds to U.S.P. antiperspirant salt concentration of 40% aluminum sesquichlorohydrate. The U.S.P. method for calculating aluminum antiperspirant salt concentrations utilizes the following formula:

% Antiperspirant Salt Concentration=Al({26.98x+ [17.01(3x−1)]+35.453}/26.98x)

where Al=concentration of aluminum and x=Al/Cl atomic ratio.

TABLE 3

Results of 40% PAC Electrodialysis

| | | Peak | | | Ratio | Peak |
|---|---|---|---|---|---|---|
| Example | Basicity | 5 | 4 | 3 | 4:3 | 4 & 5 |
| 1 | 40% | 98% | 2% | | | 100% |
| 2 | 57% | 80% | 18% | 2% | 8.38 | 98% |
| 3 | 61% | 76% | 20% | 4% | 5.26 | 96% |
| 4 | 65% | 71% | 23% | 6% | 3.62 | 94% |
| 5 | 72% | 64% | 25% | 12% | 2.10 | 88% |
| 6 | 75% | 53% | 35% | 12% | 2.84 | 88% |
| 7 | 78% | 37% | 32% | 31% | 1.04 | 69% |
| 8* | 72% | 58% | 26% | 16% | 1.61 | 84% |

*Sample was aged for two months. FIG. 9A is an HPLC of the freshly prepared material. FIG. 9B is an HPLC of the same sample two months later.

In another example 40% PAC was subjected to the electrodialysis process of the present invention. On this occasion the electrodialysis process was conducted at 60° C. The process was continued until the basicity reached 72%. Analysis by HPLC demonstrated that the product was a Group 2 Material composed of 4.5% Peak 3 materials, 48% Peak 4 materials and 47.5% Peak 5 materials. The Peak 4 plus Peak 5 composition was 95.5%; indicating once again a low molecular weight composition was produced. The Peak 4 to Peak 3 ratio was 10.7. The $Al_2O_3$ concentration of the product was 13.6 corresponding to a U.S.P. antiperspirant salt concentration of 35% of aluminum sesquichlorohydrate.

There are at least four approaches for the production of aluminum-zirconium antiperspirant salts using the electrodialysis processes of the present invention.

In the first instance, zirconium-hydroxychloride and glycine is combined with high basicity PAC that is prepared by electrodialysis under conditions taught by the present invention. For example, a Group 2 aluminum zirconium tetrachlorohydrate with an aluminum to zirconium ratio of 4 to 1 and metal to chloride ratio of 0.90 to 0.96 is produced when PAC with basicity of 70.4% to 73.3% (produced by the electrodialysis process of the present invention) is combined with zirconium oxychloride (ZrOCl2) and glycine. And a Group 2 aluminum-zirconium octachlorohydrate with an aluminum to zirconium ratio of 8 to 1 and metal to chloride ratio of 0.90 to 0.96 is produced when PAC with basicity of 66.7% to 69.3% (produced by the electrodialysis process of the present invention) is combined with zirconium oxychloride (ZrOCl2) and glycine. Other useful compositions will be apparent to those experienced in the art.

In the second instance, zirconium hydroxyl-chloride is combined with high basicity PAC that is prepared by electrodialysis under conditions taught by the present invention in the presence of glycine. Table 4 shows samples prepared by adding zirconium oxychloride to high basicity PAC prepared by electrodialysis of 40% PAC in the presence of glycine. Aluminum zirconium tetrachlorohydrate is formed in these examples. The Peak 5 composition is greater than 45% and the Peak 4 plus Peak 5 composition is greater than 60% in both examples, indicating that this approach is useful for making Group 2 Materials.

TABLE 4

Electrodialysis of 40% PAC & Glycine with post addition of zirconium oxychloride[1]

| Basicity[2] | Peak | | | Peak 4:3 | Peak 4 + Peak 5 |
|---|---|---|---|---|---|
| Al Only | 5 | 4 | 3 | Ratio | Area |
| 75% | 69% | 6% | 25% | 0.23 | 75% |
| 83% | 51% | 23% | 26% | 0.91 | 74% |

[1] The aluminum to zirconium atomic ratio in these examples is 4:1
[2] Basicity Al Only is based on the chemical formula 2Al2(OH)mCl6-m using the definition that basicity is m/(total of the aluminum valence)

In the third instance, PAC is combined with zirconium tetrachloride and or zirconium-hydroxychloride and or zirconium carbonates and used as a feedstock for the electrodialysis of the present invention. Glycine is optionally added upon the completion of the electrodialysis process.

Table 5 shows the results of the electrodialysis of 40% PAC with zirconium oxychloride. In this case the Peak 5 composition remains well above 45% through the entire range of basicities. The Peak 4 plus Peak 5 composition also remains well above 60% through the entire range of basicities. Thus, the electrodialysis of PAC with zirconium-hydroxychloride yields Group 2 aluminum-zirconium antiperspirant salts.

TABLE 5

Results of the 40% PAC & ZrOCl2 Electrodialysis

| M:Cl Ratio[1] | Basicity[3] Al + ZR | Basicity[2] Al Only | Peak 5 | Peak 4 | Peak 3 | Peak 1 & 2 | Peak 4:3 Ratio | Peak 4 + Peak 5 Area |
|---|---|---|---|---|---|---|---|---|
| 0.54 | 43% | 40% | 98% | 2% | 2% | 0% | 0.89 | 99% |
| 0.63 | 50% | 50% | 97% | 1% | 2% | 0% | 0.76 | 98% |
| 0.74 | 58% | 60% | 97% | 2% | 1% | 0% | 1.10 | 99% |
| 0.81 | 61% | 65% | 81% | 4% | 4% | 11% | 1.14 | 85% |
| 0.89 | 65% | 70% | 79% | 6% | 4% | 11% | 1.43 | 85% |
| 1.00 | 69% | 75% | 75% | 8% | 4% | 11% | 1.95 | 83% |
| 1.25 | 75% | 83% | 71% | 8% | 4% | 11% | 1.89 | 79% |

[1] M:Cl Ratio is the metal (Al + Zr) to chloride ratio.
[2] Basicity Al Only is based on the chemical formula $2Al_2(OH)_mCl_{6-m}$ using the definition that basicity is m/(total of the aluminum valence)
[3] Basicity Al + Zr is based on the chemical formula $2Al_2(OH)_mCl_{6-m} \cdot ZrOCl2$ using the definition that basicity is m/(total of the metal valence). In this case m is the amount of OH associated with both aluminum and zirconium.

Glycine is widely used in aluminum-zirconium antiperspirant salts. Table 6 shows the result of combining glycine with the last two samples in Table 5. Again Group 2 aluminum-zirconium antiperspirant salts are produced.

TABLE 6

Comparison to Al—Zr Electrodialysis Products Before and After Glycine Addition

| Sample | M:Cl Ratio | Basicity* Al + Zr | Basicity* Al Only | Peak 5 | Peak 4 | Peak 3 | Peak 1 & 2 | Peak 4:3 Ratio | Peak 4 + Peak 5 Area |
|---|---|---|---|---|---|---|---|---|---|
| Glycine Added | 1.00 | 69% | 75% | 79% | 6% | 6% | 9% | 1.08 | 85% |
| No Glycine | 1.00 | 69% | 75% | 74% | 8% | 6% | 12% | 1.39 | 82% |
| Glycine Added | 1.24 | 75% | 83% | 75% | 8% | 6% | 11% | 1.29 | 83% |
| No Glycine | 1.24 | 75% | 83% | 67% | 10% | 7% | 16% | 1.49 | 77% |

Figure 10:
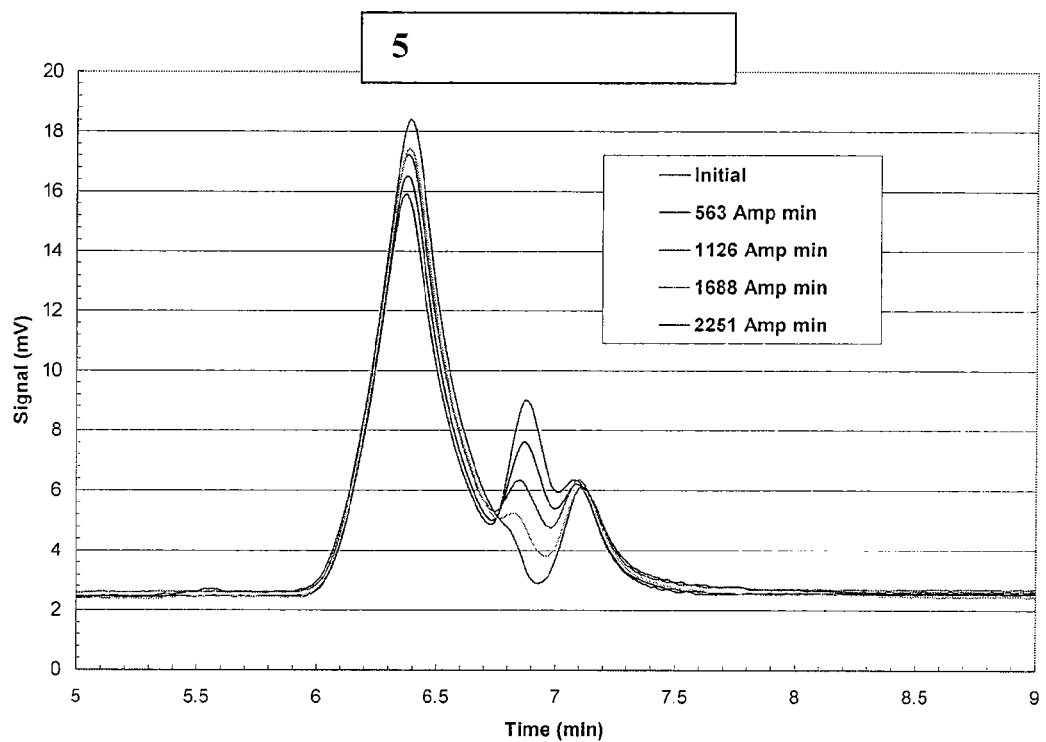
FIG. 10 is a HPLC analysis of aluminum-zirconium tetrachlorohydrate-glycine of the present invention. This chromatogram shows the progression of increasing the basicity and demonstrates that the molecular species distribution is unchanged as the basicity (i.e., the metal to chloride ratio) is increased.

In the fourth instance, PAC is combined with zirconium tetrachloride and or zirconium-hydroxychloride and or zirconium carbonate and glycine. Said aluminum-zirconium glycine combination is then used as a feedstock for the electrodialysis processes of the present invention. In this instance unique compositions are obtained. When 40% PAC is combined with zirconium oxychloride and glycine and subjected to electrodialysis according to the teachings of the present invention, the product is composed exclusively of Peak 5 material. FIG. 10 shows the HPLC analysis as the electrodialysis process proceeds. During the entire process, only the presence of Peak 5 is detected. (The two small peaks with longer retention time in this figure are glycine and hydrochloric acid). The final product in this example was an U.S.P. aluminum zirconium tetrachlorohydrate with the following formula $Al_{3.4}Zr(OH)_{9.5}Cl_{4.7} \cdot 9Gly$ (wherein Al:Zr=3.4, and M:Cl=0.94).

Thus, it has been found that the disadvantages associated with the known methods to produce antiperspirant salts containing aluminum and the antiperspirant salts containing aluminum and zirconium are generally overcome by utilizing electrodialysis to increase the basicity of aluminum salts and or aluminum zirconium salt combinations. Although the processes of the present invention can be used to produce aluminum and aluminum-zirconium compounds with a wide range of basicities, and Al:Zr ratios, there is particular interest in the ability of the processes of the present invention to produce antiperspirant salt compositions as defined by the Official Monographs of the United States Pharmacopeia. Thus, a preferred aluminum antiperspirant salt compositions salt taught by the present invention is ACH, a basic aluminum chloride with aluminum to chloride ratio between about 1.91:1 to about 2.10:1 or aluminum sesquichlorohydrate, a basic aluminum chloride with aluminum to chloride ratio of about 1.26 to about 1.90. And a preferred aluminum zirconium antiperspirant salt compositions salt taught by the present invention is an aluminum zirconium chlorohydrate, more preferably an aluminum zirconium tetrachlorohydrate (Al:Zr=about 2 to about 6; M:Cl=about 0.9 to about 1.5) or aluminum zirconium octachlorohydrate (Al:Zr=about 6 to about 10; M:Cl=about 0.9 to about 1.5) or aluminum zirconium pentachlorohydrate (Al:Zr=about 6 to about 10; M:Cl=about 2.1 to about 1.5) or aluminum zirconium trichlorohydrate (Al:Zr=about 2.0 to about 5.99; M:Cl=about 2.1 to about 1.5).

Also of particular interest are the various compositions of aluminum antiperspirant salt Group 2 Materials and the aluminum-zirconium antiperspirant salt Group 2 Materials produced.

The present invention is detailed in the following paragraphs, For example paragraph 1, provides a method to increase the hydroxide content of compounds comprising

(Compound I)

wherein M is a metal that undergoes the reaction:

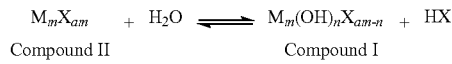

wherein "a" is the valence of the metal ion;
X is an anion;
$0 < n \leq am$;
$m \geq 1$;
comprising the step of subjecting a solution of Compound I to electrodialysis conditions to generate HX or subjecting a solution of Compound II to electrodialysis, wherein Compound II subsequently hydrolyzes to form Compound I with generation of HX, such that the hydroxide content of Compound I is increased relative to the hydroxide content of the initial Compound I.

2. The method of paragraph 1, wherein the depleting solution and receiving solution are both composed of Compounds I, such that the HX concentration is decreased from the depleting solution, thereby providing Compound I in the depleting stream with increased hydroxide content relative to initial Compound I prior to treatment.

3. The method of paragraph 1, wherein initial Compound I and/or Compound II are freshly prepared and or subjected to heat treatment prior to or during the electrodialysis process.

4. The method of paragraph 1, wherein the receiving solution from the electrodialysis process is reacted with aluminum trihydrate and reused in the electrodialysis process.

5. The method of paragraph 1, wherein the depleting solution has a concentration of aluminum ion greater than 1 molar.

6. The method of paragraph 1, wherein the products have a basicity greater than 50%

7. The method of paragraph 1, wherein M is Al such that the aluminum to halide ratio is between about 1.9:1 to about 2.1:1.

8. The method of paragraph 1, wherein M is Al, such that the aluminum to halide ratio is between about 1.26 to about 1.90.

9. The method of paragraph 1, wherein M is Ti.

10. The method of paragraph 1, wherein M is Zr.

11. The method of paragraph 1, wherein M is Fe.

12. The method of any of paragraphs 1 through 6, wherein X is a halide.

13. The method of any of paragraphs 7 through 11, wherein the halide is chloride.

14. The method of paragraph 1, wherein a combination of Compounds I and or Compounds II having different M's are mixed prior to, during or after the electrodialysis process, whereby HX is generated and removed from the depleting solution such that a binary or mixed metal hydroxychloride is formed.

15. The method of paragraph 14, wherein the first M is Al and the second M is Zr.

16. The method of paragraph 15, wherein the metal hydroxychloride complex produced is aluminum zirconium tetrachlorohydrate (Al:Zr=between about 2 to about 6; M:Cl=between about 0.9 to about 1.5) or aluminum zirconium octachlorohydrate (Al:Zr=between about 6 to about 10; M:Cl=between about 0.9 to about 1.5) or aluminum zirconium pentachlorohydrate (Al:Zr=between about 6 to about 10; M:Cl=between about 2.1 to about 1.5) or aluminum zirconium trichlorohydrate (Al:Zr=between about 2.0 to about 5.99; M:Cl=between about 2.1 to about 1.5).

17. The method of any of paragraphs 1, 7, 8 and 14 through 16, wherein the products have enhanced efficacy properties.

18. The method of any of the paragraphs 1, 7, 8 and 14 through 16, further comprising amino acids, organic acids and polyols.

19. The method of paragraph 18, wherein the amino acid is selected from the group consisting of glycine, alanine, valine, serine, leucine and aminobutyric acid.

20. The method of paragraph 18, wherein the organic acid is selected from the group consisting of gluconic acid, oxalic acid and citric acid.

21. The method of paragraph 18, wherein the polyols is selected from the group consisting of glycols.

22. The method of any of paragraphs 1, 7, 8 and 14 through 16 further comprising compounds that prevent aluminum and or aluminum zirconium complexes from gelling and are incorporated within the metal hydroxychloride complex.

23. The method of either paragraphs 18 or 19, wherein said amino acids are incorporated as their corresponding alkali metal salt, or their alkaline earth metal salt, aluminum salt or their ammonium salt.

24. The method of paragraph 1, further comprising calcium ions that are incorporated in the amount of greater than 0% and less than 2%; wherein the calcium ions may be incorporated prior to, during or after the electrodialysis process.

25. The method of paragraph 15, wherein the zirconium has the general formula $Zr(OH)_{4-b}X_b$ wherein X is Cl, Br, I, or $NO_3$, and b is about 0.7 to about 4.0.

26. The method of paragraph 25, wherein X is Cl.

27. The method of paragraph 25, wherein the material is zirconium oxychloride or zirconium hydroxychloride.

28. The method of paragraph 25, wherein the zirconium salts include 1 to 8 moles of water of hydration per mole of salt.

29. The method of any of paragraphs 1, 7, 14 and 18 through 21 further comprising organic solvents incorporated into the product.

30. The method of paragraph 29, wherein the organic solvent contains at least two carbons and at least one hydroxyl group selected from the group consisting of ethanol, propanol, iso-propanol, and butanol.

In another aspect, the present invention in a 31$^{st}$ paragraph provides a polyaluminum halide (PAH) comprising aluminum, hydroxide and a halide; wherein when analyzed by HPLC, the PAH exhibits a peak area of peak 5 of greater than 50% and or a combined peak area of peak 5 and peak 4 of at least 70%.

32. An antiperspirant composition comprising a dermatologically acceptable carrier and a perspiration reducing effective amount of a PAC of paragraph 31.

33. The PAH of either paragraphs 31 or 32 in solid powder form.

34. The PAH of either paragraphs 31 or 32 in an aqueous composition comprising water.

35. The PAH of any of paragraphs 31 through 34 further comprising an amino acid.

36. The PAH of paragraph 35, wherein the amino acid is selected from glycine, valine, alanine, lysine, arginine, mixtures and salts thereof.

37. The PAH of paragraph 35, wherein the amino acid is glycine.

In still another aspect, the present invention in a 38$^{th}$ paragraph provides an aluminum-zirconium halohydrate comprising: aluminum, zirconium, hydroxide and halide; wherein, when analyzed by HPLC, the aluminum-zirconium halohydrate exhibits an HPLC peak 5 area of at least 80% and an HPLC peak 4 to peak 3 ratio of less than 0.15.

39. The aluminum-zirconium halohydrate of paragraph 38, wherein the metal (Al/Zr) to chloride ratio is about 0.9 to about 2.1.

40. The aluminum-zirconium halohydrate of either paragraphs 38 or 39, wherein the halide is chloride.

In still another aspect, the present invention provides in a 41$^{st}$ paragraph, an aluminum-zirconium halohydrate comprising: aluminum, zirconium, hydroxide and halide; wherein, when analyzed by HPLC the aluminum-zirconium halohydrate exhibits essentially only an HPLC peak 5.

42. The aluminum-zirconium halohydrate of paragraph 41, wherein peaks 4 and 3 are substantially undetectable.

43. The aluminum-zirconium halohydrate of paragraph 41, wherein peaks 4 and 3 are not present.

44. The aluminum-zirconium halohydrate of any of paragraphs 41 through 43, wherein the Al to Zr ratio is about 2.0 to about 10

45. The aluminum-zirconium halohydrate of any of paragraphs 41 through 44, wherein the halide is chloride.

46. The aluminum-zirconium chlorohydrate of any of paragraphs 41 through 45 further comprising an amino acid.

47. The aluminum-zirconium chlorohydrate of paragraph 46, wherein the amino acid is selected from glycine, valine, alanine, lysine, arginine and salts thereof.

48. The aluminum-zirconium chlorohydrate of paragraph 47, wherein the amino acid is glycine.

49. An antiperspirant composition comprising a dermatologically acceptable carrier and a perspiration reducing effective amount of an aluminum-zirconium chlorohydrate of any of paragraphs 41 through 48.

50. The aluminum-zirconium chlorohydrate of any of paragraphs 41 through 48 in solid powder form.

51. The aluminum-zirconium chlorohydrate of any of paragraphs 41 through 48 in an aqueous form.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

EXAMPLES

Description of HPLC Analysis: The methods for performing size exclusion HPLC analysis are well documented in the literature. The current work utilized procedures similar to those described the following references: U.S. Pat. No. 6,649, 152, U.S. Pat. No. 5,955,064, and U.S. Pat. No. 6,149,897. The specific instrumentation, column, and conditions used in the present work are described below:

Instrument: Waters 510 HPLC Pump, Waters 717 Autosampler, Waters 410 differential Refractometer, Millennium Version 3.20 Software.

Column: Phenomenex Luna 5μ Silica (2) 100 A, 250×4.6 mm.

Mobile Phase: $HNO_3$ at pH 2.2, 0.5 ml/minute.

Instrument Parameters: Mobile Phase Flow at 0.5 mL/minute isocratic, RI detector temperature at 30° C., column temperature at 35° C., 10 μL injection.

Sample Preparation: Samples are diluted 100 fold in mobile phase prior to injection.

The electrodialysis experiments were carried out in a Eurodia EUR6-15 electrodialysis stack. The stack consisted of a DSE anode and cathode and a combination of Neosepta AHA anion permeable membrane and Neosepta CMX cation permeable membranes. There were 15 ED membrane pairs each with an operating surface area of 0.056 m². The feed (PAC) compartment consisted of a 14 liter glass reservoir and an Iwaki centrifugal circulating pump. Inlet pressure, flow, temperature, pH, and solution conductivity were monitored during the runs.

The receiving loop consisted of a 14 liter glass reservoir and an Iwaki centrifugal circulating pump. The inlet pressure, pH and temperature of this solution were also monitored during the runs. The electrode rinse loop consisted of a 15 liter polypropylene reservoir and an Iwaki centrifugal circulating pump. The electrode rinse solution (0.5% $H_2SO_4$) was split into two streams before entering the anode and cathode compartments. The solutions exiting the compartments were recombined in the main reservoir. It was anticipated that this configuration would maintain a constant pH in the rinse solution.

Power was supplied to the stack by two Sorensen DCS 20-50 DC power supplies connected in series. Selected data was collected during the runs (e.g., current, depleting solution and receiving solution pH, depleting solution conductivity, depleting solution and receiving solution temperature and depleting solution flow and charge passed) and several samples of each stream were taken for later analysis.

Example 1

Preparation of Enhanced Efficacy Aluminum Antiperspirant Salts Compositions

Description of Electrodialysis Stack: The electrodialysis stack used in this example was a Eurodia 6. In this example there were twenty membrane pairs. The stack is designed to operate up to 65° C. The stack was configured with Astom membranes. The cation exchange membranes were CMX (cation exchange membrane) and the anion exchange membranes were AHA (anion exchange membrane). Both of these membranes are compatible with operation up to 65° C.

10 Liters of 40% PAC was diluted with 10 liters of deionized water. The solution was agitated and heated to 90° C. The solution was held at this temperature for 1 hour and then topped off with deionized water back to a total volume of 20 liters. After cooling to 60° C., the resulting solution was fed to the electrodialysis stack as the depleting solution as described below.

The enriching solution was approximately 2 M $CaCl_2$ solution (6 liters). The enriching solution compartments were equipped with an apparatus that allowed for the addition of $Ca(OH)_2$ in order to maintain the pH at a value of 0.5 or greater during the course of the run. The depleting solution was also heated to and maintained at a temperature of 60° C. during the course of the run.

Circulation of the enriching and depleting solutions was begun and a potential gradient of about 14 volts was applied to the cell (~0.4 volts per membrane pair); the current density was limited to 50 $mA/cm^2$. The current efficiency was 65%.

At the end of the run the depleting solution had a volume of 11.6 liters and was analyzed to contain 13.6% $Al_2O_3$. (or 3.3 Molar on an aluminum basis) with 71.7% basicity. The product produced was $Al_2(OH)_{4.3}Cl_{1.7}$. Analysis by HPLC demonstrated the product was composed of 4.5% Peak 3, 48% Peak 4 and 47.5% Peak 5. The Peak 4 to Peak 3 ratio was 10.7

Example 2

Preparation of Enhanced Efficacy Aluminum Antiperspirant Salts Compositions

Electrodialysis Stack: Eurodia 6 (15 membrane pairs)
Temperature: 65° C.
Membranes: Neosepta CMX and AHA
Starting Materials:
Depleting Solution: 40% PAC
Enriching Solution: 40% PAC
Heat Treatment of the Depleting Solution: 5 Liters of 40% PAC (~17.1% $Al_2O_3$) was diluted with 4.3 Liters of water; the agitated solution was heated to 90° C. The solution was held at this temperature for 1 hour and allowed to cool to 65° C. before feeding the resulting solution to the electrodialysis stack as the depleting solution as described below.

Heat Treatment of the Receiving Solution: 6.7 Liters of 40% PAC were heated to 90° C. The solution was held at this temperature for 1 hour and allowed to cool to 65° C. before feeding the resulting solution to the electrodialysis stack as the receiving solution as described below.

The depleting loop of the ED stack was charged with 9.3 Liters of the depleting solution prepared as described above. The receiving loop of the ED stack was charged with 6.7 Liters of the receiving solution prepared as described above. Circulation of the enriching and depleting solutions was begun and a potential gradient of ~16 volts was applied to the cell (0.8 volts per membrane pair). The initial current was 40 $mA/cm^2$. The current density was maintained at 40 $mA/cm^2$ and the basicity was increased to 64%. The voltage had increased to 17.99 volts at this point.

7.44 Liters of the depleting solution prepared similarly to that described above was added to the depleting loop. 4 Liters of the receiving solution prepared similarly to that described above was added to the receiving loop and the current flow was maintained. The addition of fresh solutions caused the voltage to drop and the current density returned to the level of 40 $mA/cm^2$. When the basicity of the depleting solution reached ~74%, the CD was 36 $mA/cm^2$. The run was terminated at 78% basicity and the CD at this time was 34 $mA/cm^2$. 61.9 moles of charge were passed during the experiment and the current efficiency was 82%.

Example 3

Preparation of Enhanced Efficacy Aluminum Zirconium Antiperspirant Salts Compositions Description of Electrodialysis Stack: The electrodialysis stack used in this example was a Eurodia 6. In this example there were fifteen membrane pairs. The stack is designed to operate up to 65° C. The stack was configured with Astom membranes. The cation exchange membranes were CMX (cation exchange membrane) and the anion exchange membranes were AHA (anion exchange membrane). Both of these membranes are compatible with operation up to 65° C.

Preparation of the depleting solution: Zirconium oxychloride ($ZrOCl_2.8H_2O$) 1.96 kg was dissolved in 3 L $H_2O$. Glycine 0.474 kg was added and the solution was stirred for about 1 hour. The zirconium-glycine solution was then diluted to a volume of 5 liters. Freshly prepared 40% PAC 6.85 kg (17.1% $Al_2O_3$) was heated to and maintained at 90° C. for a period of 1 hour. The hot PAC solution was slowly added with mixing to the room temperature zirconium-glycine solution, resulting in a combined solution with a temperature of about 60° C.

The receiving solution in this experiment was comprised of 8.75 kg of 40% PAC (~17.1% $Al_2O_3$), which was also heat-treated at 90° C. for a period of 1 hour. The receiving solution was cooled to about 60° C. and both the depleting and the receiving solutions were charged to the Eurodia 6.

Circulation of the enriching and depleting solutions was begun and a potential gradient of about 18 volts was applied to the cell (~0.8 volts per membrane pair); the current density was limited to 40 $mA/cm^2$.

The experiment was terminated after passage of 2251 Amp min. The analysis of the depleting solution is shown in the table below. The results demonstrate that the 40% PAC was converted to $Al_{3.4}Zr(OH)_{9.5}Cl_{4.7}$.Gly having a metal to chloride ratio of 0.94 and a basicity of 64.5% (based on the OH to total metal valence ratio). The current efficiency was 88%.

| Charge mol | Volume L | Density g/L | $Al_2O_3$ M | $Al_2O_3$ % | Zirconium M | Chloride M | Basicity % |
|---|---|---|---|---|---|---|---|
| 0.0 | 9.78 | 1.27 | 1.05 | 8.4 | 0.60 | 4.86 | 44.0% |
| 21.0 | 6.75 | 1.32 | 1.45 | 11.2 | 0.86 | 4.31 | 64.3% |

HPLC analysis conducted during the experiment is shown in the FIG. 10 below and demonstrates that the peak 5 composition of the 40% PAC was maintained throughout the electrodialysis run.

Example 4

Preparation of Enhanced Efficacy Aluminum Zirconium Antiperspirant Salts Compositions Electrodialysis Stack: Eurodia 6 (15 membrane pairs)
Temperature 65° C.
Membranes: Neosepta CMX and AHA
Starting Materials:
Depleting Solution: 40% PAC and Zirconium Oxychloride
Enriching Solution: 40% PAC
Preparation of the Depleting Solution: 4 Liters of 40% PAC (~17.1% $Al_2O_3$) was diluted with 4 Liters of water; the agitated solution was heated to 90° C. The solution was held at this temperature for 1 hour and allowed to cool to 65° C. The solution was then diluted with 1.57 Kg of zirconium oxychloride octahydrate diluted to a volume of 4 L. The resulting solution to the electrodialysis stack as the depleting solution as described below.

Preparation of the Receiving Solution: The receiving solution used in this experiment was 8.6 L of 40% PAC ((~17.1% $Al_2O_3$) diluted with 1 L of water. The receiving solution was not heat treated in this example.

The depleting loop and the receiving loop of the ED stack were charged the appropriate solutions prepared as described above and circulation of the solutions was begun. A potential gradient of 14 volts was applied to the cell (0.7 volts per membrane pair). The initial current was 40 mA/cm². The current density was maintained at 40 mA/cm² and the aluminum basicity was increased to 83%. The voltage had increased to 16 volts at this point. A total of 25.9 moles of charge was passed during this experiment. Solution analysis showed the product of the electrodialysis was aluminum zirconium tetrachlorohydrate with an Al:Zr ratio of 3.3 and a M:Cl ratio of 0.94, corresponding to a formula of $Al_{3.3}Zr(OH)_{9.3}Cl_{4.5}$.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claim.

We claim:

1. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \qquad\qquad \text{Compound (I)}$$

wherein "a" is the valence of the metal ion;
X is an anion;
$0 < n \leq am$;
$m \geq 1$;
comprising the step of subjecting a solution of Compound I to electrodialysis conditions to generate HX, such that the hydroxide content of Compound I is increased relative to the initial hydroxide content of Compound I, provided that
  i. enriching and depleting streams both comprise a Compound of formula I; and
  ii. a combination of Compounds I having different M's are mixed prior to, during, or after the electrodialysis process, such that a mixed metal product is formed.

2. The method of claim 1, wherein the product has a basicity greater than 50%.

3. The method of claim 1, wherein at least one M is Al.

4. The method of claim 1, wherein at least one M is Ti.

5. The method of claim 1, wherein at least one M is Zr.

6. The method of claim 1, wherein at least one M is Fe.

7. The method of claim 1, wherein at least one X is a halide.

8. The method of claim 7, wherein the halide is chloride.

9. The method of claim 1, wherein a first M is Al and a second M is Zr.

10. The method of claim 9, wherein the mixed metal product is aluminum zirconium tetrachlorohydrate (Al:Zr=between about 2 to about 6; M:Cl=between about 0.9 to about 1.5) or aluminum zirconium octachlorohydrate (Al:Zr=between about 6 to about 10; M:Cl=between about 0.9 to about 1.5) or aluminum zirconium pentachlorohydrate (Al:Zr=between about 6 to about 10; M:Cl=between about 2.1 to about 1.5) or aluminum zirconium trichlorohydrate (Al:Zr=between about 2.0 to about 5.99; M:Cl=between about 2.1 to about 1.5).

11. The method of claim 9, wherein the zirconium has the general formula $Zr(OH)_{4-b}X_b$ wherein X is Cl, Br, I, or $NO_3$, and b is about 0.7 to about 4.0.

12. The method of claim 11, wherein X is Cl.

13. The method of claim 11, wherein the material is zirconium oxychloride or zirconium hydroxychloride.

14. The method of claim 11, wherein the zirconium salts include 1 to 8 moles of water of hydration per mole of salt.

15. The method of claim 1, wherein the mixed metal product has enhanced efficacy properties.

16. The method of claim 1, further comprising calcium ions that are incorporated in the amount of greater than 0% and less than 2%; wherein the calcium ions may be incorporated during the electrodialysis process.

17. The method of claim 1, wherein the mixed metal product has enhanced efficacy properties.

18. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \qquad\qquad \text{Compound (I)}$$

wherein "a" is the valence of the metal ion;
X is an anion;
$0 < n \le am$;
$m \ge 1$;
comprising the step of subjecting a solution of Compound I to electrodialysis conditions to generate HX, such that the hydroxide content of Compound I is increased relative to the initial hydroxide content of Compound I, further comprising the step of adding an amino acid, an organic acid or a polyol to the depleting or receiving stream during the electrodialysis process provided that
  i. enriching and depleting streams both comprise a Compound of formula I; and
  ii. a combination of Compounds I having different M's are mixed prior to, during, or after the electrodialysis process, such that a mixed metal product is formed.

19. The method of claim 18, wherein the amino acid is selected from the group consisting of glycine, alanine, valine, serine, leucine and aminobutyric acid.

20. The method of claim 18, wherein the organic acid is selected from the group consisting of gluconic acid, oxalic acid and citric acid.

21. The method of claim 18, wherein the polyol is selected from the group consisting of glycols.

22. The method of claim 18, further comprising compounds that prevent aluminum and or aluminum zirconium complexes from gelling and are incorporated within the metal complexes.

23. The method of claim 18, wherein said amino acids are incorporated as their corresponding alkali metal salt, or their alkaline earth metal salt, aluminum salt or their ammonium salt.

24. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \qquad\qquad \text{Compound (I)}$$

wherein "a" is the valence of the metal ion;
X is an anion;
$0 < n \le am$;
$m \ge 1$;
comprising the step of subjecting a solution of Compound I to electrodialysis conditions to generate HX, such that the hydroxide content of Compound I is increased relative to the initial hydroxide content of Compound I, further comprising organic solvents incorporated into the product provided that
  i. enriching and depleting streams both comprise a Compound of formula I; and
  ii. a combination of Compounds I having different M's are mixed prior to, during, or after the electrodialysis process, such that a mixed metal product is formed.

25. The method of claim 24, wherein the organic solvent contains at least two carbons and at least one hydroxyl group selected from the group consisting of ethanol, propanol, isopropanol, and butanol.

26. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \qquad\qquad \text{Compound (I)}$$

wherein "a" is the valence of the metal ion;
X is an anion;
$0 < n \le am$;
$m \ge 1$;
comprising the step of subjecting a solution of Compound I to electrodialysis conditions to generate HX, such that the hydroxide content of Compound I is increased relative to the hydroxide content of the initial Compound I to provide a product, provided that
  i. enriching and depleting streams both comprise a Compound of formula (I), wherein the product is an enhanced efficacy material.

27. The method of claim 26, wherein the product has a basicity greater than 50%.

28. The method of claim 26, wherein M is Al.

29. The method of claim 26, wherein M is Ti.

30. The method of claim 26, wherein M is Zr.

31. The method of claim 26, wherein M is Fe.

32. The method of claim 26, wherein at least one X is a halide.

33. The method of claim 32, wherein the halide is chloride.

34. The method of claim 26, further comprising calcium ions that are incorporated in the amount of greater than 0% and less than 2%; wherein the calcium ions may be incorporated during the electrodialysis process.

35. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \qquad\qquad \text{Compound (I)}$$

wherein "a" is the valence of the metal ion;
X is an anion;
$0 < n \le am$;
$m \ge 1$;
comprising the step of subjecting a solution of Compound I to electrodialysis conditions to generate HX, such that the hydroxide content of Compound I is increased relative to the hydroxide content of the initial Compound I to provide a product, further comprising the step of adding an amino acid, an organic acid or a polyol to the depleting or receiving stream during the electrodialysis process provided that i. enriching and depleting streams both comprise a Compound of formula (I), wherein the product is an enhanced efficacy material.

36. The method of claim 35, wherein the amino acid is selected from the group consisting of glycine, alanine, valine, serine, leucine and aminobutyric acid.

37. The method of claim 35, wherein the organic acid is selected from the group consisting of gluconic acid, oxalic acid and citric acid.

38. The method of claim 35, wherein the polyol is selected from the group consisting of glycols.

39. The method of claim 35, further comprising compounds that prevent aluminum or zirconium complexes from gelling and are incorporated within the metal complexes.

40. The method of claim 35, wherein said amino acids are incorporated as their corresponding alkali metal salt, or their alkaline earth metal salt, aluminum salt or their ammonium salt.

41. A method to increase the hydroxide content of compounds comprising the formula (I):

$$M_m(OH)_nX_{am-n} \quad \text{(Compound I)}$$

wherein M is a metal that undergoes the reaction:

$$M_mX_{am} + H_2O \rightleftharpoons M_m(OH)_nX_{am-n} + HX$$
$$\text{Compound (II)} \quad\quad\quad\quad \text{Compound (I)}$$

wherein "a" is the valence of the metal ion;
X is an anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I to provide a product, further comprising organic solvents incorporated into the product provided that
  i. enriching and depleting streams both comprise a Compound of formula (I), wherein the product is an enhanced efficacy material.

42. The method of claim 41, wherein the organic solvent contains at least two carbons and at least one hydroxyl group selected from the group consisting of ethanol, propanol, isopropanol, and butanol.

43. A method to increase the hydroxide content of compounds comprising the formula (I):

$$M_m(OH)_nX_{am-n} \quad \text{(Compound I)}$$

wherein M is a metal selected from Al, Ti, Zr or Fe that undergoes the reaction:

$$M_mX_{am} + H_2O \rightleftharpoons M_m(OH)_nX_{am-n} + HX$$
$$\text{Compound (II)} \quad\quad\quad\quad \text{Compound (I)}$$

wherein "a" is the valence of the metal ion;
X is any monovalent anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, provided that
  i. enriching and depleting streams both comprise a Compound of formula (I);
  ii. a combination of Compounds I having different M's are mixed prior to, during, or after the electrodialysis process, such that a mixed metal product is formed; and
  iii. wherein the pH of the enriching stream is less than a pH of 2.

44. The method of claim 43, wherein the product has a basicity greater than 50%.

45. The method of claim 43, wherein at least one M is Al.

46. The method of claim 43, wherein at least one M is Ti.

47. The method of claim 43, wherein at least one M is Zr.

48. The method of claim 47, wherein the zirconium has the general formula $Zr(OH)_{4-b}X_b$ wherein X is Cl, Br, I, or $NO_3$, and b is about 0.7 to about 4.0.

49. The method of claim 48, wherein X is Cl.

50. The method of claim 48, wherein the material is zirconium oxychloride or zirconium hydroxychloride.

51. The method of claim 48, wherein the zirconium salts include 1 to 8 moles of water of hydration per mole of salt.

52. The method of claim 43, wherein at least one M is Fe.

53. The method of claim 43, wherein at least one X is a halide.

54. The method of claim 43, wherein the halide is chloride.

55. The method of claim 43, wherein a first M is Al and a second M is Zr.

56. The method of claim 55, wherein the mixed metal product is aluminum zirconium tetrachlorohydrate (Al:Zr=between about 2 to about 6; M:Cl=between about 0.9 to about 1.5) or aluminum zirconium octachlorohydrate (Al:Zr=between about 6 to about 10; M:Cl=between about 0.9 to about 1.5) or aluminum zirconium pentachlorohydrate (Al:Zr=between about 6 to about 10; M:Cl=between about 2.1 to about 1.5) or aluminum zirconium trichlorohydrate (Al:Zr=between about 2.0 to about 5.99; M:Cl=between about 2.1 to about 1.5).

57. The method of claim 43, further comprising calcium ions that are incorporated in the amount of greater than 0% and less than 2%; wherein the calcium ions may be incorporated during the electrodialysis process.

58. The method of claim 43, wherein the mixed metal product has enhanced efficacy properties.

59. A method to increase the hydroxide content of compounds comprising the formula (I):

$$M_m(OH)_nX_{am-n} \quad \text{(Compound I)}$$

wherein M is a metal selected from Al, Ti, Zr or Fe that undergoes the reaction:

$$M_mX_{am} + H_2O \rightleftharpoons M_m(OH)_nX_{am-n} + HX$$
$$\text{Compound (II)} \quad\quad\quad\quad \text{Compound (I)}$$

wherein "a" is the valence of the metal ion;
X is any monovalent anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, further comprising the step of adding an amino acid, an organic acid or a polyol to the depleting or receiving stream during the electrodialysis provided that i. enriching and depleting streams both comprise a Compound of formula (I);
ii. a combination of Compounds I having different M's are mixed prior to, during, or after the electrodialysis process, such that a mixed metal product is formed; and
iii. wherein the pH of the enriching stream is less than a pH of 2.

60. The method of claim 59, wherein the amino acid is selected from the group consisting of glycine, alanine, valine, serine, leucine and aminobutyric acid.

61. The method of claim 59, wherein the organic acid is selected from the group consisting of gluconic acid, oxalic acid and citric acid.

62. The method of claim 59, wherein the polyol is selected from the group consisting of glycols.

63. The method of claim 59, further comprising compounds that prevent aluminum and or aluminum zirconium complexes from gelling and are incorporated within the metal complexes.

64. The method of claim 59, wherein said amino acids are incorporated as their corresponding alkali metal salt, or their alkaline earth metal salt, aluminum salt or their ammonium salt.

65. A method to increase the hydroxide content of compounds comprising the formula (I):

$$M_m(OH)_n X_{am-n} \quad \text{(Compound I)}$$

wherein M is a metal selected from Al, Ti, Zr or Fe that undergoes the reaction:

$$M_m X_{am} + H_2O \rightleftharpoons M_m(OH)_n X_{am-n} + HX$$
Compound (II)       Compound (I)

wherein "a" is the valence of the metal ion;
X is any monovalent anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, wherein the organic solvent contains at least two carbons and at least one hydroxyl group selected from the group consisting of ethanol, propanol, iso-propanol, and butanol provided that
i. enriching and depleting streams both comprise a Compound of formula (I);
ii. a combination of Compounds I having different M's are mixed prior to, during, or after the electrodialysis process, such that a mixed metal product is formed; and
iii. wherein the pH of the enriching stream is less than a pH of 2.

66. The method of claim 65, wherein the organic solvent contains at least two carbons and at least one hydroxyl group selected from the group consisting of ethanol, propanol, iso-propanol, and butanol.

67. A method to increase the hydroxide content of compounds comprising the formula (I):

$$M_m(OH)_n X_{am-n} \quad \text{(Compound I)}$$

wherein M is a metal that undergoes the reaction:

$$M_m X_{am} + H_2O \rightleftharpoons M_m(OH)_n X_{am-n} + HX$$
Compound (II)       Compound (I)

wherein "a" is the valence of the metal ion;
X is an anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, provided that
i. enriching and depleting streams both comprise a Compound of formula (I);
ii. wherein the pH of the enriching stream is less than a pH of 2, wherein the product is an enhanced efficacy material.

68. The method of claim 67, wherein the product has a basicity greater than 50%.

69. The method of claim 67, wherein M is Al.

70. The method of claim 67, wherein M is Ti.

71. The method of claim 67, wherein M is Zr.

72. The method of claim 67, wherein M is Fe.

73. The method of claim 67, wherein at least one X is a halide.

74. The method of claim 73, wherein the halide is chloride.

75. The method of claim 67, further comprising calcium ions that are incorporated in the amount of greater than 0% and less than 2%; wherein the calcium ions may be incorporated during the electrodialysis process.

76. A method to increase the hydroxide content of compounds comprising the formula (I):

$$M_m(OH)_n X_{am-n} \quad \text{(Compound I)}$$

wherein M is a metal that undergoes the reaction:

$$M_m X_{am} + H_2O \rightleftharpoons M_m(OH)_n X_{am-n} + HX$$
Compound (II)       Compound (I)

wherein "a" is the valence of the metal ion;
X is an anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, further comprising the step of adding an amino acid, an organic acid or a polyol to the depleting or receiving stream during the electrodialysis process provided that
i. enriching and depleting streams both comprise a Compound of formula (I);
ii. wherein the pH of the enriching stream is less than a pH of 2, wherein the product is an enhanced efficacy material.

77. The method of claim 76, wherein the amino acid is selected from the group consisting of glycine, alanine, valine, serine, leucine and aminobutyric acid.

78. The method of claim 76, wherein the organic acid is selected from the group consisting of gluconic acid, oxalic acid and citric acid.

79. The method of claim 76, wherein the polyol is selected from the group consisting of glycols.

80. The method of claim 76, further comprising compounds that prevent aluminum or zirconium complexes from gelling and are incorporated within the metal complexes.

81. The method of claim 76, wherein said amino acids are incorporated as their corresponding alkali metal salt, or their alkaline earth metal salt, aluminum salt or their ammonium salt.

82. A method to increase the hydroxide content of compounds comprising the formula (I):

         (Compound I)

wherein M is a metal that undergoes the reaction:

wherein "a" is the valence of the metal ion;
X is an anion;
$0 < n \leq am$;
$m \geq 1$;
comprising the step of subjecting a solution of Compound I to electrodialysis conditions to generate HX, such that the hydroxide content of Compound I is increased relative to the hydroxide content of the initial Compound I, further comprising organic solvents incorporated into the product provided that
  i. enriching and depleting streams both comprise a Compound of formula (I);
  ii. wherein the pH of the enriching stream is less than a pH of 2, wherein the product is an enhanced efficacy material.

83. The method of claim 82, wherein the organic solvent contains at least two carbons and at least one hydroxyl group selected from the group consisting of ethanol, propanol, isopropanol, and butanol.

* * * * *